US010119977B2

(12) United States Patent
Nath et al.

(10) Patent No.: US 10,119,977 B2
(45) Date of Patent: Nov. 6, 2018

(54) THERAPEUTIC AND DIAGNOSTIC METHODS FOR AUTISM SPECTRUM DISORDERS AND OTHER CONDITIONS

(71) Applicant: THE JOHNS HOPKINS UNIVERSITY, Baltimore, MD (US)

(72) Inventors: Avindra Nath, Ellicott City, MD (US); Tongguang Wang, Lutherville, MD (US); Christina Michelle Morris-Berry, Baltimore, MD (US); Harvey Singer, Baltimore, MD (US)

(73) Assignee: The Johns Hopkins University, Balimore, MD (US)

( * ) Notice: Subject to any disclaimer, the term of this patent is extended or adjusted under 35 U.S.C. 154(b) by 0 days.

(21) Appl. No.: 15/136,021

(22) Filed: Apr. 22, 2016

(65) Prior Publication Data
US 2016/0334413 A1 Nov. 17, 2016

Related U.S. Application Data

(63) Continuation of application No. 13/926,539, filed on Jun. 25, 2013, now abandoned.
(60) Provisional application No. 61/663,743, filed on Jun. 25, 2012.

(51) Int. Cl.
| | |
|---|---|
| G01N 33/53 | (2006.01) |
| G01N 33/566 | (2006.01) |
| A61K 38/00 | (2006.01) |
| C12Q 1/68 | (2018.01) |
| G01N 33/68 | (2006.01) |
| A61K 31/4184 | (2006.01) |
| A61K 31/4525 | (2006.01) |
| A61K 31/7105 | (2006.01) |
| C07K 16/28 | (2006.01) |

(52) U.S. Cl.
CPC ..... *G01N 33/6854* (2013.01); *A61K 31/4184* (2013.01); *A61K 31/4525* (2013.01); *A61K 31/7105* (2013.01); *G01N 33/6893* (2013.01); *C07K 16/2869* (2013.01); *C07K 2317/10* (2013.01); *C07K 2317/21* (2013.01); *C07K 2317/73* (2013.01); *C07K 2317/75* (2013.01); *G01N 2333/705* (2013.01); *G01N 2333/726* (2013.01); *G01N 2800/30* (2013.01); *G01N 2800/50* (2013.01)

(58) Field of Classification Search
None
See application file for complete search history.

(56) References Cited

U.S. PATENT DOCUMENTS

| | | |
|---|---|---|
| 5,196,444 A | 3/1993 | Naka et al. |
| 5,834,432 A | 11/1998 | Rodgers et al. |
| 7,604,948 B2 | 10/2009 | Amaral et al. |

FOREIGN PATENT DOCUMENTS

| | | |
|---|---|---|
| WO | 2001001987 A1 | 1/2001 |
| WO | 2009106470 A2 | 9/2009 |

OTHER PUBLICATIONS

Plioplys, A., et al., "Anti-GNS antibodies in childhood neurologic diseases", Neuropaediatrics. May 1989; 20(2):93-102.
Singer, H., et al., "Antibrain antibodies in children with autism and their unaffected siblings", Journal of neuroimmunology. Sep. 2006; 178:149-55.
Singh, V., et al., "Circulating autoantibodies to neuronal and glial filament proteins in autism", Pediatr Neural. Jul. 1997;17(1):88-90.
Todd, R., et al., "Demonstration of inter- and intraspecies differences in serotonin binding sites by antibodies from an autistic child", Proc Natl Acad Sci U S A Jan. 1985; 82(2): 612-616.
Dalton, P., et al., "Maternal neuronal antibodies associated with autism and a language disorder", Ann Neural. Apr. 2003;53(4):533-7.
Vincent, A., et al., "Antibodies to neuronal targets in neurological and psychiatric diseases", Ann N Y Acad Sci. May 2003;992:48-55.
Braunschweig, D., et al., "Autism: maternally derived antibodies specific for fetal brain proteins", Neurotoxicology. Mar. 2008; 29(2): 226-231.
Singer, H., et al., "Antibodies against fetal brain in sera of mothers with autistic children", J Neuroimmunol. Feb. 2008;194:165-72.
Singer, H., et al., "Prenatal exposure to antibodies from mothers of children with autism produces neurobehavioral alterations: A pregnant dam mouse model", J Neuroimmunol. Jun. 2009 25;211:39-48.
Hollander, E., et al., "A double-blind placebo-controlled trial of fluoxetine for repetitive behaviors and global severity in adult autism spectrum disorders", Am J Psychiatry. Mar. 2012;169(3):292-9.
Cabanlit, M., et al., "Brain-specific autoantibodies in the plasma of subjects with autistic spectrum disorder", Ann N Y Acad Sci. Jun. 2007;1107:92-103.
Silva, S., et al., "Autoantibody repertoires to brain tissue in autism nuclear families", J Neuroimmunol. Jul. 2004;152:176-82.
Zimmerman, A., et al., "Maternal antibrain antibodies in autism. Brain, behavior and immunity", vol. 21, Issue 3, Mar. 2007, pp. 351-357.
Pelliccia, F., et al., "Angiotensin II receptor antagonism with telmisartan increases number of endothelial progenitor cells in normotensive patients with coronary artery disease: A randomized, double-blind, placebo-controlled study", Atherosclerosis, (2010) 210(2), pp. 510-515.

(Continued)

*Primary Examiner* — Olga N Chernyshev
(74) *Attorney, Agent, or Firm* — Johns Hopkins Technology Ventures

(57) ABSTRACT

The present invention relates to the field of autism. More specifically, the present invention provides methods for treating individuals with autism spectrum disorders. The present invention also provides methods for predicting a likelihood of ASD. In one embodiment, a method for treating a female patient having a high risk factor of having children with ASD comprises the steps of (a) identifying in a sample taken from the female patient the presence of AT-1 antibodies; and (b) administering an effective amount of an AT-1 inhibitor or inhibitor of AT-1 antibodies to the female patient.

4 Claims, 9 Drawing Sheets

(56) References Cited

OTHER PUBLICATIONS

Mitra, A, et al., "Angiotensin II-induced upregulation of AT1 receptor expression: sequential activation of NF-κB and Elk-1 in neurons", American Journal of Physiology—Cell Physiology. Sep. 1, 2010, 2010;299(3):C561-C9.

Min, L., et al., "Angiotensin II and aldosterone-induced neuronal damage in neurons through an astrocyte-dependent mechanism", Hypertens Res. 2011;34(6):773-8.

Wu, X., et al., "Angiotensin receptor type 1 antagonists protect against neuronal injury induced by oxygen-glucose depletion", British Journal of Pharmacology. 2010;161(1):33-50.

Lou, M., et al., "Sustained Blockade of Brain AT1 Receptors Before and After Focal Cerebral Ischemia Alleviates Neurologic Deficits and Reduces Neuronal Injury, Apoptosis, and Inflammatory Responses in the Rat", J Cereb Blood Flow Metab. 2004;24(5):536-47.

Saavedra, J., et al., "Blockade of brain angiotensin II AT1 receptors ameliorates stress, anxiety, brain inflammation and ischemia: Therapeutic implications", Psychoneuroendocrinology. 2011;36(1):1-18.

Zhang, S., et al., "Angiotensin type 1 receptor autoantibody from preeclamptic patients induces human fetoplacental vasoconstriction", Journal of Cellular Physiology. (2013) 228: 142-148.

Kolevzon, A., et al., "Selective serotonin reuptake inhibitors in autism: a review of efficacy and tolerability", J Clin Psychiatry. Mar. 2006;67(3):407-14.

Comi, A.M., et al., Familial clustering of autoimmune disorders and evaluation of medical risk factors in autism. J Child Neurol, 1999. 14(6): p. 388-94.

Rodriguez-Palleros, J., et al., Brain angiotensin enhances dopaminergic cell death via microglial activation and NADPH-derived ROS. Neurobiology of Disease, 2008. 31(1): p. 58-73.

Lee, L.C., et al., HLA-DR4 in families with autism. Pediatr Neurol, 2006. 35(5): p. 303-7.

Rogers, T., et al., Exclusion of linkage to the HLA region in ninety multiplex sibships with autism. J Autism Dev Disord, 1999. 29(3): p. 195-201.

Torres, A.R., et al., The transmission disequilibrium test suggests that HLA-DR4 and DR13 are linked to autism spectrum disorder. Hum Immunol, 2002. 63(4): p. 311-6.

Croen, L.A., et al., Maternal autoimmune diseases, asthma and allergies, and childhood autism spectrum disorders: a case-control study. Arch Pediatr Adolesc Med, 2005. 159(2): p. 151-7.

Molloy, C.A., et al., Familial autoimmune thyroid disease as a risk factor for regression in children with Autism Spectrum Disorder: a CPEA Study. J Autism Dev Disord, 2006. 36(3): p. 317-24.

Sweeten, T.L., et al., Increased prevalence of familial autoimmunity in probands with pervasive developmental disorders. Pediatrics, 2003. 112(5): p. e420.

Arvidsson, A., et al., Neuronal replacement from endogenous precursors in the adult brain after stroke. Nat Med, 2002. 8(9): p. 963-70.

Hallbergson, A.F., et al. Neurogenesis and brain injury: managing a renewable resource for repair. J Clin Invest, 2003. 112(8): p. 1128-33.

Miyazaki, K, N. Narita, and M. Narita, Maternal administration of thalidomide or valproic acid causes abnormal serotonergic neurons in the offspring: implication for pathogenesis of autism. Int J Dev Neurosci, 2005. 23(2-3): p. 287-97.

Ingram, J.L., et al., Discovery of allelic variants of HOXA1 and HOXB1: genetic susceptibility to autism spectrum disorders. Teratology, 2000. 62(6): p. 393-405.

Martinez-Cabellos, E. et al. Hoxa1 is required for the retinoic acid-induced differentiation of embryonic stem cells into neurons. J Neurosci Res, 2008. 86(13): p. 2809-19.

Li, H. et al., Transcription factor MEF2C influences neural stem/progenitor cell differentiation and maturation in vivo. Proc Natl Acad Sci U S A, 2008. 105(27): p. 9397-402.

Wang, T., et al., Activated T-cells inhibit neurogenesis by releasing granzyme B: rescue by Kv1.3 blockers. J Neurosci, 2010. 30(14): p. 5020-7.

Morris, C.M., A.W. Zimmerman, and H.S. Singer, Childhood serum anti-fetal brain antibodies do not predict autism. Pediatr Neurol, 2009.41(4): p. 288-90.

Vargas D.L., et al., Neuroglial activation and neuroinflammation in the brain of patients with autism. Annals of Neurology, 2005. 57(1): p. 67-81.

Thomas, M.A., et al., Subcellular identification of angiotensin I/II- and angiotensin II (AT1)-receptor-immunoreactivity in the central nervous system of rats. Brain Research, 2003. 962(1-2): p. 92-104.

Imanishi, T. et al. Angiotensin II potentiates vascular endothelial growth factor-induced proliferation and network formation of endothelial progenitor cells. Hypertens Res, 2004.27(2): p. 101-8.

Sumners, C., et al., Angiotensin II type 1 receptor modulation of neuronal K+ and Ca2+ currents: intracellular mechanisms. Am J Physiol, 1996. 271(1 Pt 1): p. C154-63.

Aguilera, G., et al. Increased expression of type 1 angiotensin II receptors in the hypothalamic paraventricular nucleus following stress and glucocorticoid administration. J Neuroendocrinol, 1995. 7(10): p. 775-83.

THERAPEUTIC AND DIAGNOSTIC METHODS FOR AUTISM SPECTRUM DISORDERS AND OTHER CONDITIONS

CROSS-REFERENCE TO RELATED APPLICATIONS

This application is a Continuation of U.S. application Ser. No. 13/926,539, filed Jun. 25, 2013, which claims the benefit of U.S. Provisional Application No. 61/663,743, filed Jun. 25, 2012, the content of each of the aforementioned applications is herein incorporated by reference in their entirety.

STATEMENT OF GOVERNMENTAL INTEREST

This invention was made with government support under grant number R01NS056884, awarded by the National Institutes of Health. The government has certain rights in the invention.

FIELD OF THE INVENTION

The present invention relates to the field of autism. More specifically, the present invention provides methods for treating individuals with autism spectrum disorders.

BACKGROUND OF THE INVENTION

The autism spectrum disorders (ASD) affect as many as 1 in 88 children in the United States and comprise a broad group of behaviorally related neurodevelopmental disorders that include autism, Asperger's disorder, pervasive developmental disorder-not otherwise specified (PDD-NOS), Rett's syndrome and childhood disintegrative disorder. The hallmark features of ASD appear around three years of age as impaired social and communication interactions, pronounced repetitive behaviors and restricted pattern of interests. There continues to be a need for treatments for autistic individuals.

SUMMARY OF THE INVENTION

The present invention is based, at least in part, on the discovery that maternal antibodies from mothers of children with autistic disorders (MCAD-IgG) targets Angiotensin II type 1 (AT-1) receptor on neural progenitor cells (NPC) to inhibit neuronal genesis and increase astrogliosis. In addition, it was found that modulation of AT-1 receptor using antagonists reverses the effects of MCAD-IgG on the NPC. Accordingly, AT-1 plays an important role in modulating neurogenesis and represents a therapeutic target for autism and in other disorders where neuorgenesis may be impaired.

Indeed, in certain embodiments, modulation of the AT-1 function using antibodies or other specific inhibitor can be used as a therapy for autism and for other disorders where neurogenesis is impaired. In another embodiment, a therapeutic approach can include the removal of AT-1 antibodies (MCAD-IgG) from blood. Antibodies can be removed via plasmaphoresis, which exchanges the antibodies with other components in plasma, or immunophoresis, which removes antibodies only.

In yet another embodiment, pharmacological or biological agents can be used to antagonize the effects of the AT-1 antibody. Currently, an FDA approved drug Telmisartan is available and an antagonist to the AT-1 receptor. However, other antagonists with different pharmacological properties can also be used. In further embodiments, an AT-1 receptor mimic can be used. These compounds bind to the AT-1 antibody and neutralize it before it has the opportunity to activate the AT-1 receptor.

The therapeutic methods of the present invention can be used for treating the mother prior to pregnancy or during pregnancy. In alternative embodiments, the methods can be used to treat an infant who displays the presence of these antibodies.

In one embodiment, a method for treating a female patient having a high risk factor of having children with ASD comprises the steps of (a) identifying in a sample taken from the female patient the presence of AT-1 antibodies; and (b) administering an effective amount of an AT-1 inhibitor or inhibitor of AT-1 antibodies to the female patient. In a specific embodiment, the female patient is pregnant. In particular embodiments, the ASD is selected from the group consisting of autism, Asperger's disorder, pervasive developmental disorder-not otherwise specified (PDD-NOS), Rett's syndrome and childhood disintegrative disorder.

In further embodiments, the AT-1 inhibitor or inhibitor of AT-1 antibodies is an inhibitor selected from the group consisting of a small molecule, an antibody, an aptamer, and an inhibitory nucleic acid molecule. In a specific embodiment, the inhibitor is a small molecule. In a more specific embodiment, the small molecule is Telmisartan.

The methods can further comprise administering an effective amount of a selective serotonin reuptake inhibitor (SSRI). For example, the SSRI can be, but is not limited to, fluoxetine, fluvoxamine, paroxetine, sertraline or mianserin. In a specific embodiment, the SSRI is paroxetine.

The present invention also provides a method for treating a female patient having a high risk factor of having children with ASD comprising the step of administering an effective amount of an AT-1 inhibitor to the patient, wherein the female patient has AT-1 antibodies present in her blood. In an alternative embodiments, the present invention provides a method for treating a female patient having a high risk factor of having children with ASD comprising the steps of (a) identifying in a sample taken from the female patient the presence of AT-1 antibodies; and (b) performing plasmaphoresis or immunophoresis on the female patient to remove the AT-1 antibodies.

In a further embodiment, a method for treating or preventing the development of ASD in an infant comprises the step of administering an effective amount of AT-1 inhibitor or inhibitor of AT-1 antibodies. In yet another embodiment, the present invention provides a method for treating a patient having an ASD comprising the step of administering to the patient an effective amount of an AT-1 inhibitor or inhibitor of AT-1 antibodies.

In another aspect, the AT-1 antibodies described herein (MCAD-IgG) can be used as a diagnostic tool. In specific embodiments, the appearance of AT-1 specific antibody in maternal serum is likely a high risk factor and can be used as a marker for diagnosis/prognosis.

In another specific embodiment, a method of screening a female patient for a high risk of having children with an autism spectrum disorder (ASD) comprises the steps of (a) obtaining a sample from the female patient; (b) detecting the presence of antibodies specific for angiotensin II type 1 receptor (AT-1) in the sample; and (c) identifying the female patients as having a high risk of having children with ASD if the AT-1 antibodies are present. In certain embodiments, the female patient is pregnant. In other embodiments, the female patient is not pregnant.

In certain embodiments, the detecting step is performed using mass spectrometry. In an alternative embodiment, the detecting step comprises the steps of (a) contacting the sample obtained from the female patient with an AT-1 polypeptide; and (b) detecting the binding of the AT-1 polypeptide with the AT-1 antibodies, wherein the detection of binding id indicative of the presence of AT-1 antibodies in the sample. In a more specific embodiment, the binding is detected by enzyme-linked immunosorbent assay (ELISA), immunoprecipitation or immunoblotting. In further embodiments, the method further comprises the step of administering to the female patient an effective amount of an AT-1 inhibitor or an inhibitor of the AT-1 antibodies.

In another specific embodiment, a method of screening a female patient for a high risk of having children with ASD comprises the steps of (a) obtaining a sample from the female patient; (b) detecting the presence of antibodies specific for angiotensin II type 1 receptor (AT-1) in the sample using an immunoassay or mass spectrometry; and (c) identifying the female patients as having a high risk of having children with ASD if the AT-1 antibodies are present.

DETAILED DESCRIPTION OF THE INVENTION

Figure 1A:
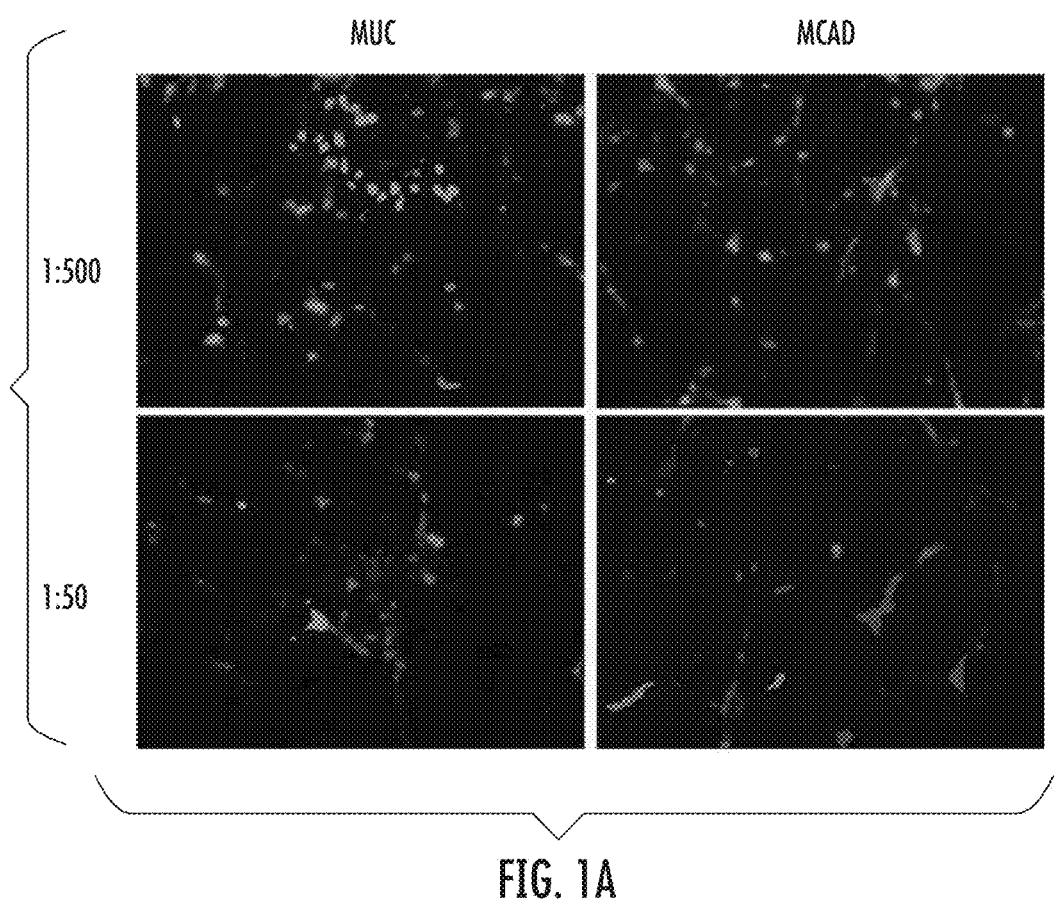
FIG. 1A. MCAD-IgG inhibits NSC proliferation: The effect of MCAD-IgG on NSC proliferation was studied by exposing cultured human NSC in maintaining media on PDL-coated cover slips to corresponding concentrations (1:500 to 1:50) of MCAD or MUC antibodies 24 hours with added BrdU solution in the culture media for the last 6 hours. BrdU immunostaining was performed on the cover slips (BrdU positive cells (red) and DAPI positive cells (blue)).
Figure 1B:
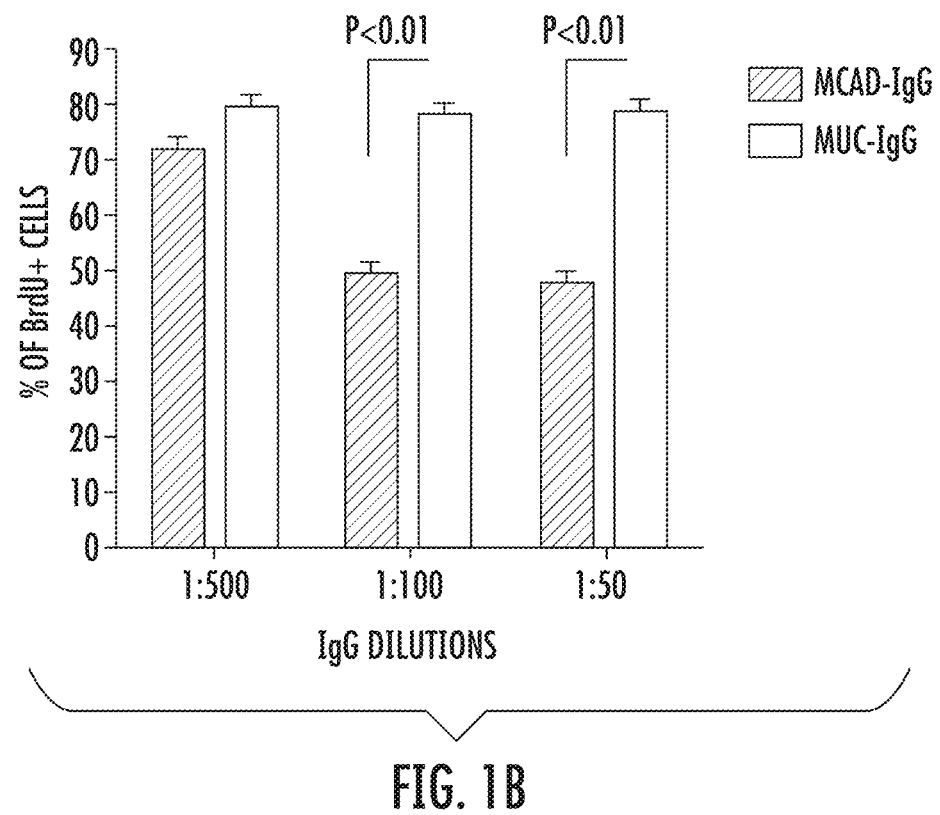
FIG. 1B. BrdU incorporation was determined by calculating the percentage of BrdU positive cells in DAPI positive cells.

It is understood that the present invention is not limited to the particular methods and components, etc., described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to a "protein" is a reference to one or more proteins, and includes equivalents thereof known to those skilled in the art and so forth.

Unless defined otherwise, all technical and scientific terms used herein have the same meaning as commonly understood by one of ordinary skill in the art to which this invention belongs. Specific methods, devices, and materials are described, although any methods and materials similar or equivalent to those described herein can be used in the practice or testing of the present invention.

All publications cited herein are hereby incorporated by reference including all journal articles, books, manuals, published patent applications, and issued patents. In addition, the meaning of certain terms and phrases employed in the specification, examples, and appended claims are provided.

Autism is a neural development disorder affecting social interaction and communication in children. Although etiology is still unknown, immune dysfunction may play a role in the development of the disease. Maternal IgG from Mothers of Children with Autistic Disorder (MCAD-IgG)

cross reacts with specific brain proteins however, its significance remains unknown. In present study, we investigated the effect of MCAD-IgG on functions of neural stem cells (NSC).

As further described herein, we treated primary cultured human fetal NSC with MCAD-IgG and determined its effects on cell viability, proliferation and differentiation. Cell viability was studied using cellquantiblue assay and active caspase-3 immunostaining. NSC proliferation was studied by BrdU incorporation assay and neural differentiation was studied by neuronal marker, beta-III tubulin and astroglial marker, GFAP immunostaining and Western-blot analysis. Targets on cell membrane that react with MCAD-IgG were studied by co-immunoprecipitation.

Compared to maternal antibodies from mothers with normal children (MUC-IgG), MCAD-IgG (at 1:50 dilution) showed no significant effect on cell death and apoptosis. However, MCAD-IgG significantly decreased NSC proliferation and neuronal differentiation but increased astroglial differentiation. Further studies showed that the angiotensin II receptor 1 (AT-1) was immunoprecipitated by MCAD-IgG and pretreatment with AT-1specific inhibitor, telmisartan, attenuated MCAD-IgG-mediated effects on NSC differentiation. MCAD-IgG effects on NSC neural differentiation were also attenuated by pretreatment with a selective serotonin reuptake inhibitor (SSRI), paroxetine.

Thus, MCAD-IgG impairs NSC neurogenesis by targeting AT-1, which may contribute to the pathogenesis of autism. AT-1 antagonists or SSRI may be used to treat MCAD-IgG-mediated effects on NSC. These findings provide novel insight into autism and may be used for developing therapeutic interventions.

I. DEFINITIONS

The definitions are not meant to be limiting in nature and serve to provide a clearer understanding of certain aspects of the present invention.

As used herein, the term "modulate" indicates the ability to control or influence directly or indirectly, and by way of non-limiting examples, can alternatively mean inhibit or stimulate, agonize or antagonize, hinder or promote, and strengthen or weaken. Thus, the term "AT-1 modulator" refers to an agent that modulates angiotensin II type 1 receptor. Modulators may be organic or inorganic, small to large molecular weight individual compounds, mixtures and combinatorial libraries of inhibitors, agonists, antagonists, and biopolymers such as peptides, nucleic acids, or oligonucleotides. A modulator may be a natural product or a naturally-occurring small molecule organic compound. In particular, a modulator may be a carbohydrate; monosaccharide; oligosaccharide; polysaccharide; amino acid; peptide; oligopeptide; polypeptide; protein; receptor; nucleic acid; nucleoside; nucleotide; oligonucleotide; polynucleotide including DNA and DNA fragments, RNA and RNA fragments and the like; lipid; retinoid; steroid; glycopeptides; glycoprotein; proteoglycan and the like; and synthetic analogues or derivatives thereof, including peptidomimetics, small molecule organic compounds and the like, and mixtures thereof. A modulator identified according to the invention is useful in the treatment of a disease disclosed herein.

As used herein, an "antagonist" is a type of modulator and the term refers to an agent directly or indirectly inhibits one or more functions/effects of a target protein. In certain embodiments, an antagonist agent binds a target (e.g., a protein) and can inhibit one or more functions of the target. For example, an antagonist of a protein can bind the protein and inhibit the binding of a natural or cognate ligand to the protein and/or inhibit signal transduction mediated through the protein. In other embodiments, an antagonist interacts with an upstream or downstream component of a target protein in a pathway and inhibits one or more functions of the target protein (e.g., AT-1). The term "antagonist" is used interchangeably with the term "inhibitor."

An "agonist" is a type of modulator and refers to an agent that directly or indirectly activates or increases one or more functions/effects of a target protein. In certain embodiments, an agonist agent binds a target and can activate or increase one or more functions/effects of the target. For example, an agonist of a target protein can bind the protein and activate the target protein in the absence of its natural or cognate ligand/binding partner. In other embodiments, an agonist interacts with an upstream or downstream component of a target protein in a pathway and activates or increases one or more functions/effects of the target protein.

As used herein, the term "antibody" is used in reference to any immunoglobulin molecule that reacts with a specific antigen. It is intended that the term encompass any immunoglobulin (e.g., IgG, IgM, IgA, IgE, IgD, etc.) obtained from any source (e.g., humans, rodents, non-human primates, caprines, bovines, equines, ovines, etc.). Specific types/examples of antibodies include polyclonal, monoclonal, humanized, chimeric, human, or otherwise-human-suitable antibodies. "Antibodies" also includes any fragment or derivative of any of the herein described antibodies. In specific embodiments, antibodies may be raised against AT-1 and used as AT-1 modulators.

As used herein, the term "antigen" is generally used in reference to any substance that is capable of reacting with an antibody. It is intended that this term encompass any antigen and "immunogen" (i.e., a substance which induces the formation of antibodies). Thus, in an immunogenic reaction, antibodies are produced in response to the presence of an antigen (immunogen) or portion of an antigen. More specifically, the terms are used herein to describe an antigen that elicits a humoral and/or cellular immune response (i.e., is immunogenic), such that administration of the immunogen to an animal (e.g., via a vaccine) mounts an antigen-specific immune response against the same or similar antigens that are encountered within the tissues of the animal. In another embodiment, when it is desirable to suppress an immune response against a given antigen, an antigen may comprise a toleragen.

The terms "specifically binds to," "specific for," and related grammatical variants refer to that binding which occurs between such paired species as antibody/antigen, enzyme/substrate, receptor/agonist, and lectin/carbohydrate which may be mediated by covalent or non-covalent interactions or a combination of covalent and non-covalent interactions. When the interaction of the two species produces a non-covalently bound complex, the binding which occurs is typically electrostatic, hydrogen-bonding, or the result of lipophilic interactions. Accordingly, "specific binding" occurs between a paired species where there is interaction between the two which produces a bound complex having the characteristics of an antibody/antigen or enzyme/substrate interaction. In particular, the specific binding is characterized by the binding of one member of a pair to a particular species and to no other species within the family of compounds to which the corresponding member of the binding member belongs. Thus, for example, an antibody typically binds to a single epitope and to no other epitope within the family of proteins. In some embodiments, specific binding between an antigen and an antibody will have a binding affinity of at least $10^{-6}$ M. In other embodiments, the antigen and antibody will bind with affinities of at least $10^{-7}$ M, $10^{-8}$ M to $10^{-9}$ M, $10^{-10}$ M, $10^{-11}$ M, or $10^{-12}$ M.

Optional" or "optionally" means that the subsequently described event or circumstance can or cannot occur, and that the description includes instances where the event or circumstance occurs and instances where it does not.

As used herein, a "subject" or "patient" means an individual and can include domesticated animals, (e.g., cats, dogs, etc.); livestock (e.g., cattle, horses, pigs, sheep, goats, etc.), laboratory animals (e.g., mouse, rabbit, rat, guinea pig, etc.) and birds. In one aspect, the subject is a mammal such as a primate or a human. In particular, the term also includes mammals diagnosed with an autism spectrum disorder including, but not limited to, autism, Asperger's disorder, pervasive developmental disorder-not otherwise specified (PDD-NOS), Rett's syndrome and childhood disintegrative disorder. The terms also refers to mammals diagnosed with a disease, disorder or condition where neurogenesis is impaired. Further, the term refers to mammals diagnosed with an AT-1 mediated disease, disorder or condition.

As used herein, the term "effective," means adequate to accomplish a desired, expected, or intended result. More particularly, a "therapeutically effective amount" as provided herein refers to an amount of an AT-1 modulator of the present invention, either alone or in combination with another therapeutic agent, necessary to provide the desired therapeutic effect, e.g., an amount that is effective to prevent, alleviate, or ameliorate symptoms of disease or prolong the survival of the subject being treated. In a specific embodiment, the term "therapeutically effective amount" as provided herein refers to an amount of an AT-1 modulator, necessary to provide the desired therapeutic effect, e.g., an amount that is effective to prevent, alleviate, or ameliorate symptoms of disease or prolong the survival of the subject being treated. As would be appreciated by one of ordinary skill in the art, the exact amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a subject, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

The terms "AT-1-related disease, disorder or condition" or "AT-1-mediated disease, disorder or condition," and the like mean diseases, disorders or conditions associated with AT-1 signaling including, but not limited to, diseases, disorders or conditions associated with impairment of neurogenesis or in association with neurodevelopmental disorders (e.g., autism, epilepsy, etc.), neurodegenerative disorders (e.g., schizophrenia, Parkinson's, etc.) or neuronal injury. Furthermore, AT-1-related diseases, disorders or conditions include any abnormal state that involves AT-1 activity. The abnormal state can be induced by environmental exposure or drug administration. Alternatively, the disease or disorder can be due to a genetic defect.

The terms "sample," "patient sample," "biological sample," and the like, encompass a variety of sample types obtained from a patient, individual, or subject and can be used in a diagnostic or monitoring assay. The patient sample may be obtained from a healthy subject, a patient having an AT-1-related disease, disorder or condition, a patient having associated symptoms of an AT-1-related disease, disorder or condition. Moreover, a sample obtained from a patient can be divided and only a portion may be used for diagnosis. Further, the sample, or a portion thereof, can be stored under conditions to maintain sample for later analysis. The definition specifically encompasses blood and other liquid samples of biological origin (including, but not limited to, peripheral blood, serum, plasma, cerebrospinal fluid, urine, saliva, stool and synovial fluid), solid tissue samples such as a biopsy specimen or tissue cultures or cells derived therefrom and the progeny thereof. In a specific embodiment, a sample comprises a blood sample. In another embodiment, a sample comprises a plasma sample. In yet another embodiment, a serum sample is used.

The definition of "sample" also includes samples that have been manipulated in any way after their procurement, such as by centrifugation, filtration, precipitation, dialysis, chromatography, treatment with reagents, washed, or enriched for certain cell populations. The terms further encompass a clinical sample, and also include cells in culture, cell supernatants, tissue samples, organs, and the like. Samples may also comprise fresh-frozen and/or formalin-fixed, paraffin-embedded tissue blocks, such as blocks prepared from clinical or pathological biopsies, prepared for pathological analysis or study by immunohistochemistry.

As used herein, the term "comparing" refers to making an assessment of how the proportion, level or cellular localization of one or more biomarkers in a sample from a patient relates to the proportion, level or cellular localization of the corresponding one or more biomarkers in a standard or control sample. For example, "comparing" may refer to assessing whether the proportion, level, or cellular localization of one or more biomarkers in a sample from a patient is the same as, more or less than, or different from the proportion, level, or cellular localization of the corresponding one or more biomarkers in standard or control sample. More specifically, the term may refer to assessing whether the proportion, level, or cellular localization of one or more biomarkers in a sample from a patient is the same as, more or less than, different from or otherwise corresponds (or not) to the proportion, level, or cellular localization of predefined biomarker levels/ratios that correspond to, for example, a patient having an autism spectrum disorder (ASD), not having ASD, is responding to treatment for ASD, is not responding to treatment for ASD, is/is not likely to respond to a particular ASD treatment, or having/not having another disease or condition. In a specific embodiment, the term "comparing" refers to assessing whether the level of one or more biomarkers of the present invention in a sample from a patient is the same as, more or less than, different from other otherwise correspond (or not) to levels/ratios of the same biomarkers in a control sample (e.g., predefined levels/ratios that correlate to uninfected individuals, standard ASD levels/ratios, etc.).

In another embodiment, the term "comparing" refers to making an assessment of how the proportion, level or cellular localization of one or more biomarkers in a sample from a patient relates to the proportion, level or cellular localization of another biomarker in the same sample. For example, a ratio of one biomarker to another from the same patient sample can be compared. In another embodiment, a level of one biomarker in a sample (e.g., a post-translationally modified biomarker protein) can be compared to the level of the same biomarker (e.g., unmodified biomarker protein) in the sample. In a specific embodiment, the proportion of one biomarker protein can be compared to another biomarker protein, both of which are measured in the same patient sample. Ratios of biomarker proteins can be compared to other protein ratios in the same sample or to predefined reference or control ratios.

As used herein, the terms "indicates" or "correlates" (or "indicating" or "correlating," or "indication" or "correlation," depending on the context) in reference to a parameter, e.g., a modulated proportion, level, or cellular localization in a sample from a patient, may mean that the patient has a high risk factor for ASD (e.g., a high risk factor for having offspring who develop ASD or other disorder or condition in which neurogenesis is impaired). In specific embodiments, the parameter may comprise the level of one or more biomarkers of the present invention. A particular set or pattern of the amounts of one or more biomarkers may indicate that a patient has a high risk factor for ASD.

In other embodiments, a particular set or pattern of the amounts of one or more biomarkers may be correlated to a patient being unaffected (i.e., indicates a patient does not have a high risk factor for ASD). In certain embodiments, "indicating," or "correlating," as used according to the present invention, may be by any linear or non-linear method of quantifying the relationship between levels/ratios of biomarkers to a standard, control or comparative value for the assessment of the diagnosis, prediction of ASD or ASD progression, assessment of efficacy of clinical treatment, identification of a patient that may respond to a particular treatment regime or pharmaceutical agent, monitoring of the progress of treatment, and in the context of a screening assay, for the identification of an anti-ASD therapeutic.

The terms "measuring" and "determining" are used interchangeably throughout, and refer to methods which include obtaining a patient sample and/or detecting the level of a biomarker(s) in a sample. In one embodiment, the terms refer to obtaining a patient sample and detecting the level of one or more biomarkers in the sample. In another embodiment, the terms "measuring" and "determining" mean detecting the level of one or more biomarkers in a patient sample. Measuring can be accomplished by methods known in the art and those further described herein. The term "measuring" is also used interchangeably throughout with the term "detecting."

Various methodologies of the instant invention include a step that involves comparing a value, level, feature, characteristic, property, etc. to a "suitable control," referred to interchangeably herein as an "appropriate control" or a "control sample." A "suitable control," "appropriate control" or a "control sample" is any control or standard familiar to one of ordinary skill in the art useful for comparison purposes. In one embodiment, a "suitable control" or "appropriate control" is a value, level, feature, characteristic, property, etc., determined in a cell, organ, or patient, e.g., a control or normal cell, organ, or patient, exhibiting, for example, normal traits. For example, the biomarkers of the present invention may be assayed for levels/ratios in a sample from an unaffected individual (UI) or a normal control individual (NC) (both terms are used interchangeably herein). In another embodiment, a "suitable control" or "appropriate control" is a value, level, feature, characteristic, property, ratio, etc. determined prior to performing a therapy (e.g., an ASD treatment) on a patient. In yet another embodiment, a transcription rate, mRNA level, translation rate, protein level/ratio, biological activity, cellular characteristic or property, genotype, phenotype, etc., can be determined prior to, during, or after administering a therapy into a cell, organ, or patient. In a further embodiment, a "suitable control" or "appropriate control" is a predefined value, level, feature, characteristic, property, ratio, etc. A "suitable control" can be a profile or pattern of levels/ratios of one or more biomarkers of the present invention that correlates to, for example, having a high risk factor for ASD, to which a patient sample can be compared. The patient sample can also be compared to a negative control, i.e., a profile that correlates to not having ASD.

II. AT-1 AND AT-1 ANTIBODY (MCAD-IgG) MODULATORS

The present invention also provides modulators of AT-1 and AT-1 specific antibody (MCAD IgG). It is understood that, for ease of reference, reference to an AT-1 modulator herein also refers to a modulator of the AT-1 specific antibody of MCAD IgG described in the Examples.

In certain embodiments, the AT-1 modulator (or in other embodiments, a modulator of the AT-1 specific antibody that binds AT-1) is selected from the group consisting of a small molecule, a polypeptide, a nucleic acid molecule, a peptidomimetic, or a combination thereof. In a specific embodiment, the agent can be a polypeptide. The polypeptide can also comprise an antibody. In another embodiment, the agent can be a nucleic acid molecule. The nucleic acid molecule can, for example, be an AT-1 inhibitory nucleic acid molecule. The AT-1 inhibitory nucleic acid molecule can comprise a short interfering RNA (siRNA) molecule (including, for example, a short hairpin RNA (shRNA)), a microRNA (miRNA) molecule, or an antisense molecule.

As used herein, an AT-1 inhibitory nucleic acid sequence can be a siRNA sequence or a miRNA sequence. A 21-25 nucleotide siRNA or miRNA sequence can, for example, be produced from an expression vector by transcription of a short-hairpin RNA (shRNA) sequence, a 60-80 nucleotide precursor sequence, which is processed by the cellular RNAi machinery to produce either an siRNA or miRNA sequence. Alternatively, a 21-25 nucleotide siRNA or miRNA sequence can, for example, be synthesized chemically. Chemical synthesis of siRNA or miRNA sequences is commercially available from such corporations as Dharmacon, Inc. (Lafayette, Colo.), Qiagen (Valencia, Calif.), and Ambion, Inc. (Austin, Tex.). An siRNA sequence preferably binds a unique sequence within the AT-1 mRNA with exact complementarity and results in the degradation of the AT-1 mRNA molecule. An siRNA sequence can bind anywhere within the mRNA molecule. An miRNA sequence preferably binds a unique sequence within the AT-1 mRNA with exact or less than exact complementarity and results in the translational repression of the AT-1 mRNA molecule. An miRNA sequence can bind anywhere within the mRNA molecule, but preferably binds within the 3'UTR of the mRNA molecule. Methods of delivering siRNA or miRNA molecules are known in the art. See, e.g., Oh and Park, Adv. Drug Deliv. Rev. 61(10):850-62 (2009); Gondi and Rao, J. Cell. Physiol. 220(2):285-91 (2009); and Whitehead et al., Nat. Rev. Drug Discov. 8(2)129-38 (2009).

As used herein, an AT-1 inhibitory nucleic acid sequence can be an antisense nucleic acid sequence. Antisense nucleic acid sequences can, for example, be transcribed from an expression vector to produce an RNA which is complementary to at least a unique portion of the AT-1 mRNA and/or the endogenous gene which encodes AT-1. Hybridization of an antisense nucleic acid molecule under specific cellular conditions results in inhibition of AT-1 protein expression by inhibiting transcription and/or translation.

An AT-1 modulator can also be an antibody. The term antibody is used herein in a broad sense and includes both polyclonal and monoclonal antibodies. The term can also refer to a human antibody and/or a humanized antibody. Examples of techniques for human monoclonal antibody production include those described by Cole et al. (Monoclonal Antibodies and Cancer Therapy, Alan R. Liss, p. 77 (1985)) and by Boerner et al. (J. Immunol. 147(1):86-95 (1991)). Human antibodies (and fragments thereof) can also be produced using phage display libraries (Hoogenboom et al., J. Mol. Biol. 227:381 (1991); Marks et al., J. Mol. Biol. 222:581 (1991)). The disclosed human antibodies can also be obtained from transgenic animals. For example, transgenic mutant mice that are capable of producing a full repertoire of human antibodies, in response to immunization, have been described (see, e.g., Jakobovits et al., Proc. Natl. Acad. Sci. USA 90:2551-5 (1993); Jakobovits et al., Nature 362:255-8 (1993); Bruggermann et al., Year in Immunol. 7:33 (1993)).

In other embodiments, an AT-1 modulator is a small molecule. Angiotensin II type 1receptor antagonists are known in the art. See, e.g., WO2001001987, WO2009106470, and U.S. Pat. No. 5,834,432. One example of an AT-1 antagonist that can be used in the present invention is cadesartan (1-(cyclohexyloxycarbonyloxy) ethyl-2-ethoxy-1-[[2'-(1H-tetrazol-5-yl)biphen yl-4-yl] methyl]benzimidazole-7-carboxylate and the pharmaceutically acceptable salts thereof which are disclosed in U.S. Pat. No. 5,196,444).

The term "small molecule organic compounds" refers to organic compounds generally having a molecular weight less than about 5000, 4000, 3000, 2000, 1000, 800, 600, 500, 250 or 100 Daltons, preferably less than about 500 Daltons. A small molecule organic compound may be prepared by synthetic organic techniques, such as by combinatorial chemistry techniques, or it may be a naturally-occurring small molecule organic compound.

Compound libraries may be screened for AT-1 modulators. A compound library is a mixture or collection of one or more putative modulators generated or obtained in any manner. Any type of molecule that is capable of interacting with, binding or has affinity for AT-1 may be present in the compound library. For example, compound libraries screened using this invention may contain naturally-occurring molecules, such as carbohydrates, monosaccharides, oligosaccharides, polysaccharides, amino acids, peptides, oligopeptides, polypeptides, proteins, receptors, nucleic acids, nucleosides, nucleotides, oligonucleotides, polynucleotides, including DNA and DNA fragments, RNA and RNA fragments and the like, lipids, retinoids, steroids, glycopeptides, glycoproteins, proteoglycans and the like; or analogs or derivatives of naturally-occurring molecules, such as peptidomimetics and the like; and non-naturally occurring molecules, such as "small molecule" organic compounds generated, for example, using combinatorial chemistry techniques; and mixtures thereof.

A library typically contains more than one putative modulator or member, i.e., a plurality of members or putative modulators. In certain embodiments, a compound library may comprise less than about 50,000, 25,000, 20,000, 15,000, 10000, 5000, 1000, 500 or 100 putative modulators, in particular from about 5 to about 100, 5 to about 200, 5 to about 300, 5 to about 400, 5 to about 500, 10 to about 100, 10 to about 200, 10 to about 300, 10 to about 400, 10 to about 500, 10 to about 1000, 20 to about 100, 20 to about 200, 20 to about 300, 20 to about 400, 20 to about 500, 20 to about 1000, 50 to about 100, 50 to about 200, 50 to about 300, 50 to about 400, 50 to about 500, 50 to about 1000, 100 to about 200, 100 to about 300, 100 to about 400, 100 to about 500, 100 to about 1000, 200 to about 300, 200 to about 400, 200 to about 500, 200 to about 1000, 300 to about 500, 300 to about 1000, 300 to 2000, 300 to 3000, 300 to 5000, 300 to 6000, 300 to 10,000, 500 to about 1000, 500 to about 2000, 500 to about 3000, 500 to about 5000, 500 to about 6000, or 500 to about 10,000 putative modulators. In particular embodiments, a compound library may comprise less than about 50,000, 25,000, 20,000, 15,000, 10,000, 5,000, 1000, or 500 putative modulators.

A compound library may be prepared or obtained by any means including, but not limited to, combinatorial chemistry techniques, fermentation methods, plant and cellular extraction procedures and the like. A library may be obtained from synthetic or from natural sources such as for example, microbial, plant, marine, viral and animal materials. Methods for making libraries are well-known in the art. See, for example, E. R. Felder, Chimia 1994, 48, 512-541; Gallop et al., J. Med. Chem. 1994, 37, 1233-1251; R. A. Houghten, Trends Genet. 1993, 9, 235-239; Houghten et al., Nature 1991, 354, 84-86; Lam et al., Nature 1991, 354, 82-84; Carell et al., Chem. Biol. 1995, 3, 171-183; Madden et al., Perspectives in Drug Discovery and Design 2, 269-282; Cwirla et al., Biochemistry 1990, 87, 6378-6382; Brenner et al., Proc. Natl. Acad. Sci. USA 1992, 89, 5381-5383; Gordon et al., J. Med. Chem. 1994, 37, 1385-1401; Lebl et al., Biopolymers 1995, 37 177-198; and references cited therein. Compound libraries may also be obtained from commercial sources including, for example, from Maybridge, ChemNavigator.com, Timtec Corporation, ChemBridge Corporation, A-Syntese-Biotech ApS, Akos-SC, G & J Research Chemicals Ltd., Life Chemicals, Interchim S.A., and Spectrum Info. Ltd.

III. SCREENING ASSAYS

The role of AT-1 in mediating an AT-1-related disorder makes it an attractive target for agents that modulate these disorders to effectively treat, prevent, ameliorate, reduce or alleviate the disorders. Accordingly, the invention provides prescreening and screening methods aimed at identifying such agents. The prescreening/screening methods of the invention are generally, although not necessarily, carried out in vitro. Accordingly, screening assays are generally carried out, for example, using purified or partially purified components in cell lysates or fractions thereof, in cultured cells, or in a biological sample, such as a tissue or a fraction thereof or in animals.

In one embodiment, therefore, a prescreening method comprises contacting a test agent with an AT-1. Such prescreening is generally most conveniently accomplished with a simple in vitro binding assay. Means of assaying for specific binding of a test agent to a polypeptide are well known to those of skill in the art. In one binding assay, the polypeptide is immobilized and exposed to a test agent (which can be labeled), or alternatively, the test agent(s) are immobilized and exposed to the polypeptide (which can be labeled). The immobilized species is then washed to remove any unbound material and the bound material is detected. To prescreen large numbers of test agents, high throughput assays are generally preferred. Various screening formats are discussed in greater detail below.

Test agents including, for example, those identified in a prescreening assay of the invention can also be screened to determine whether the test agent affects the levels of AT-1 or RNA. Agents that reduce these levels can potentially reduce one or more AT-1 related disorders.

Accordingly, the invention provides a method of screening for an agent that modulates an AT-1 related disorder in which a test agent is contacted with a cell that expresses an AT-1 in the absence of test agent. Preferably, the method is carried out using an in vitro assay or in vivo. In such assays, the test agent can be contacted with a cell in culture or to a tissue. Alternatively, the test agent can be contacted with a cell lysate or fraction thereof (e.g., a membrane fraction for detection of AT-1). The level of (i) AT-1 or RNA is determined in the presence and absence (or presence of a lower amount) of test agent to identify any test agents that alter the level. If the level assayed is altered, the test agent is selected as a potential modulator of an AT-1 related disorder. In particular embodiments, an agent that reduces or increases the level assayed is selected as a potential modulator of one or more AT-1 related disorders.

Cells useful in this screening method include those from any of the species described above in connection with the method of reducing a drug-related effect or behavior. Cells that naturally express AT-1 are useful in these screening methods. Alternatively, cells that have been engineered to express AT-1 can be used in the method.

As noted above, screening assays are generally carried out in vitro, for example, in cultured cells, in a biological sample or fractions thereof. For ease of description, cell cultures, biological samples, and fractions are referred to as "samples" below. The sample is generally derived from an animal (e.g., any of the research animals mentioned above), preferably a mammal, and more preferably from a human.

The sample may be pretreated as necessary by dilution in an appropriate buffer solution or concentrated, if desired. Any of a number of standard aqueous buffer solutions, employing one or more of a variety of buffers, such as phosphate, Tris, or the like, at physiological pH can be used.

AT-1 can be detected and quantified by any of a number of methods well known to those of skill in the art. Examples of analytic biochemical methods suitable for detecting AT-1, include electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunohistochemistry, affinity chromatography, immunoelectrophoresis, radioimmunoassay (RIA), receptor-linked immunosorbent assays (ELISAs), immunofluorescent assays, Western blotting, fluorescence resonance energy transfer (FRET) assays, yeast two-hybrid assays, whole or partial cell current recordings, and the like. Peptide modulators may be discovered or screened for example, by phage display. See U.S. Pat. Nos. 5,096,815; 5,198,346; 5,223,409; 5,260,203; 5,403,484; 5,534,621; and 5,571,698.

Methods for identifying lead compounds for a pharmacological agent useful in the treatment of an AT-1 related disorder comprise contacting an AT-1 protein with a test compound, and measuring, for example, AT-1 expression and/or activity. The AT-1 protein may also be a modified AT-1, e.g., a chimeric and/or a deletion mutant. The AT-1 protein may be isolated or may be in a membrane or an artificial membrane. The contacting may be directly or indirectly.

Methods of the invention also include methods for screening a therapeutic agent to treat, prevent, ameliorate, reduce or alleviate an AT-1 related disorder or symptoms thereof, comprising administering a test agent to a mouse having an over-expressed AT-1 protein.

Screening for AT-1 modulatory agents can be achieved by any one of several suitable methods including, but not limited to, contacting a cell comprising the AT-1 gene or functional equivalent or derivative thereof with an agent and screening for the modulation of AT-1 protein production or functional activity, modulation of the expression of a nucleic acid molecule encoding AT-1 or modulation of the activity or expression of a downstream AT-1 cellular target. Detecting such modulation can be achieved utilizing techniques such as Western blotting, electrophoretic mobility shift assays and/or the readout of reporters of AT-1 activity such as luciferases, CAT and the like or observation of morphological changes.

The AT-1 gene or functional equivalent or derivative thereof may be naturally occurring in the cell which is the subject of testing or it may have been transfected into a host cell for the purpose of testing. Further, the naturally occurring or transfected gene may be constitutively expressed—thereby providing a model useful for, inter alia, screening for agents which down regulate AT-1 activity, at either the nucleic acid or expression product levels, or the gene may require activation—thereby providing a model useful for, inter alia, screening for agents which up regulate AT-1 expression. Further, to the extent that an AT-1 nucleic acid molecule is transfected into a cell, that molecule may comprise the entire AT-1 gene or it may merely comprise a portion of the gene such as the portion which regulates expression of the AT-1 product. For example, the AT-1 promoter region may be transfected into the cell which is the subject of testing. In this regard, where only the promoter is utilized, detecting modulation of the activity of the promoter can be achieved, for example, by ligating the promoter to a reporter gene. For example, the promoter may be ligated to luciferase or a CAT reporter, the modulation of expression of which gene can be detected via modulation of fluorescence intensity or CAT reporter activity, respectively.

In another example, the subject of detection could be a downstream AT-1 regulatory target, rather than AT-1 itself. Yet another example includes AT-1 binding sites ligated to a minimal reporter. For example, modulation of AT-1 activity can be detected by screening for the modulation of the functional activity in a cell. This is an example of an indirect system where modulation of AT-1 expression, per se, is not the subject of detection. Rather, modulation of the molecules which AT-1 regulates the expression or activity of, are monitored.

These methods provide a mechanism for performing high throughput screening of putative modulatory agents such as the test agents comprising synthetic, combinatorial, chemical and natural libraries. These methods will also facilitate the detection of agents which bind either the AT-1 nucleic acid molecule or expression product itself or which modulate the expression of an upstream molecule, which upstream molecule subsequently modulates AT-1 expression or expression product activity. Accordingly, these methods provide a mechanism for detecting agents which either directly or indirectly modulate AT-1 expression and/or activity.

Means of detecting polypeptides using electrophoretic techniques are well known to those of skill in the art (see generally, R. Scopes (1982) Polypeptide Purification, Springer-Verlag, N.Y.; Deutscher, (1990) Methods in Enzymology Vol. 182: Guide to Polypeptide Purification, Academic Press, Inc., N.Y.). A variation of this embodiment utilizes a Western blot (immunoblot) analysis to detect and quantify the presence AT-1 polypeptide(s) in the sample. This technique generally comprises separating sample polypeptides by gel electrophoresis on the basis of molecular weight, transferring the separated polypeptides to a suitable solid support (such as a nitrocellulose filter, a nylon filter, or derivatized nylon filter), and incubating the support with antibodies that specifically bind the target polypeptide(s). Antibodies that specifically bind to the target polypeptide(s) may be directly labeled or alternatively may be detected subsequently using labeled antibodies (e.g., labeled sheep anti-mouse antibodies) that specifically bind to a domain of the primary antibody.

In certain embodiments, AT-1 polypeptide(s) are detected and/or quantified in the biological sample using any of a number of well-known immunoassays (see, e.g., U.S. Pat. Nos. 4,366,241; 4,376,110; 4,517,288; and 4,837,168). For a general review of immunoassays, see also Methods in Cell Biology Volume 37: Antibodies in Cell Biology, Asai, ed. Academic Press, Inc. New York (1993); Basic and Clinical Immunology 7th Edition, Stites & Ten, eds. (1991).

Detectable labels suitable for use in the present invention include any moiety or composition detectable by spectroscopic, photochemical, biochemical, immunochemical, electrical, optical or chemical means. Examples include biotin for staining with a labeled streptavidin conjugate, magnetic beads (e.g., Dynabeads™), fluorescent dyes (e.g., fluorescein, texas red, rhodamine, coumarin, oxazine, green fluorescent protein, and the like, see, e.g., Molecular Probes, Eugene, Oreg., USA), radiolabels (e.g., 3H, 125I, 35S, 14C, or 32P), receptors (e.g., horseradish peroxidase, alkaline phosphatase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, late; etc.) beads. Patents teaching the use of such labels include U.S. Pat. Nos. 3,817,837; 3,850,752; 3,939,350; 3,996,345; 4,277,437; 4,275,149; and 4,366,241.

In certain embodiments, compositions for use in the therapeutic methods of the invention inhibit AT-1 expression and/or function by about 5%, more preferably about 7.5% or 10%, and still more preferable, at least about 20%, 30%, 40%, 50%, 60%, 70%, 80%, 90% or 100% initiation.

IV. THERAPEUTIC AND OTHER METHODS OF USE

The AT-1 modulators described herein have in vitro and in vivo diagnostic and therapeutic utilities. For example, these molecules can be administered to cells in culture, e.g., in vitro or in vivo, or in a subject, e.g., in vivo, to treat, prevent or diagnose a variety of AT-1-mediated diseases, disorders or conditions.

In one embodiment, the modulators of the invention can be used to detect levels of AT-1. This can be achieved, for example, by contacting a sample (such as an in vitro sample) and a control sample with the AT-1 modulator under conditions that allow for the formation of a complex between the modulator and AT-1. Any complexes formed between the molecule and AT-1 are detected and compared in the sample and the control. For example, standard detection methods, well known in the art, such as ELISA and flow cytometric assays, can be performed using the compositions of the invention.

Accordingly, in one aspect, the invention further provides methods for detecting the presence of AT-1 (e.g., human AT-1) in a sample, or measuring the amount of AT-1, comprising contacting the sample, and a control sample, with an AT-1 modulator (e.g., an antibody) of the invention, under conditions that allow for formation of a complex between the antibody or portion thereof and AT-1. The formation of a complex is then detected, wherein a difference in complex formation between the sample compared to the control sample is indicative of the presence of AT-1 in the sample.

The present invention also provides therapeutic methods for treating patients with autism spectrum disorders or diseases, disorders or conditions in which neurogenesis is impaired. In a specific embodiment, the AT-1 modulator is an antagonist. Currently, an FDA approved drug Telmisartan is available and an antagonist to the AT-1 receptor. However, other antagonists with different pharmacological properties could be developed.

In further embodiments, AT-1 receptor mimics can be used. In such embodiments, these compounds bind to the AT-1 specific antibody (MCAD-IgG) and neutralize it before it has the opportunity to activate the receptor. The therapeutic approaches described herein could be used for treating the mother prior to pregnancy or during pregnancy. Alternatively it might be used to treat the infant who displays the presence of these antibodies.

In another aspect, the present invention provides methods for detecting the presence and/or amount of AT-1 specific antibody in women. In certain embodiments, the detection of AT-1 specific antibodies in pregnant woman can be used as a high risk marker for children with autism. In other embodiment, the detection of AT-1 specific antibodies in women prior to pregnancy can be used as a high risk marker.

In another aspect, the present invention also provides methods for removing the AT-1 specific antibodies from blood. In exemplary embodiments, this may be in the form of plasmaphoresis that exchanges the antibodies with other components in plasma, or immunophoresis that removes antibodies only In other embodiments, pharmacological agents can be used to antagonize the effects of the AT-1 antibody.

V. PHARMACEUTICAL COMPOSITIONS AND ADMINISTRATION

Accordingly, a pharmaceutical composition of the present invention may comprise an effective amount of an AT-1 modulator. A pharmaceutical composition may comprise an effective amount of an antagonist of an AT-1 specific antibody (MCAD-IgG). As used herein, the term "effective," means adequate to accomplish a desired, expected, or intended result. More particularly, an "effective amount" or a "therapeutically effective amount" is used interchangeably and refers to an amount of an AT-1 modulator, perhaps in further combination with yet another therapeutic agent, necessary to provide the desired "treatment" (defined herein) or therapeutic effect, e.g., an amount that is effective to prevent, alleviate, treat or ameliorate symptoms of a disease or prolong the survival of the subject being treated. In particular embodiments, the pharmaceutical compositions of the present invention are administered in a therapeutically effective amount to treat patients suffering from an AT-1-mediated disease, disorder or condition (e.g., a disease, disorder or condition associated with an autism spectrum disorder or a disorder in which neurogenesis is impaired). As would be appreciated by one of ordinary skill in the art, the exact low dose amount required will vary from subject to subject, depending on age, general condition of the subject, the severity of the condition being treated, the particular compound and/or composition administered, and the like. An appropriate "therapeutically effective amount" in any individual case can be determined by one of ordinary skill in the art by reference to the pertinent texts and literature and/or by using routine experimentation.

The pharmaceutical compositions of the present invention are in biologically compatible form suitable for administration in vivo for subjects. The pharmaceutical compositions can further comprise a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which an AT-1 modulator is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water may be a carrier when the pharmaceutical composition is administered orally. Saline and aqueous dextrose may be carriers when the pharmaceutical composition is administered intravenously. Saline solutions and aqueous dextrose and glycerol solutions may be employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried slim milk, glycerol, propylene, glycol, water, ethanol and the like. The pharmaceutical composition may also contain minor amounts of wetting or emulsifying agents, or pH buffering agents.

The pharmaceutical compositions of the present invention can take the form of solutions, suspensions, emulsions, tablets, pills, capsules, powders, sustained-release formulations and the like. The composition can be formulated as a suppository, with traditional binders and carriers such as triglycerides. Oral formulation may include standard carriers such as pharmaceutical grades of mannitol, lactose, starch, magnesium stearate, sodium saccharine, cellulose, magnesium carbonate, etc. In a specific embodiment, a pharmaceutical composition comprises an effective amount of an AT-1 modulator together with a suitable amount of a pharmaceutically acceptable carrier so as to provide the form for proper administration to the patient. The formulation should suit the mode of administration.

The pharmaceutical compositions of the present invention may be administered by any particular route of administration including, but not limited to oral, parenteral, subcutaneous, intramuscular, intravenous, intrarticular, intrabronchial, intraabdominal, intracapsular, intracartilaginous, intracavitary, intracelial, intracelebellar, intracerebroventricular, intracolic, intracervical, intragastric, intrahepatic, intramyocardial, intraosteal, intraosseous, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, iontophoretic means, or transdermal means. Most suitable routes are oral administration or injection. In certain embodiments, subcutaneous injection is preferred.

In general, the pharmaceutical compositions comprising an AT-1 modulator may be used alone or in concert with other therapeutic agents at appropriate dosages defined by routine testing in order to obtain optimal efficacy while minimizing any potential toxicity. The dosage regimen utilizing a pharmaceutical composition of the present invention may be selected in accordance with a variety of factors including type, species, age, weight, sex, medical condition of the patient; the severity of the condition to be treated; the route of administration; the renal and hepatic function of the patient; and the particular pharmaceutical composition employed. A physician of ordinary skill can readily determine and prescribe the effective amount of the pharmaceutical composition (and potentially other agents including therapeutic agents) required to prevent, counter, or arrest the progress of the condition.

Optimal precision in achieving concentrations of the therapeutic regimen (e.g., pharmaceutical compositions comprising an AT-1 modulator, optionally in combination with another therapeutic agent) within the range that yields maximum efficacy with minimal toxicity may require a regimen based on the kinetics of the pharmaceutical composition's availability to one or more target sites. Distribution, equilibrium, and elimination of a pharmaceutical composition may be considered when determining the optimal concentration for a treatment regimen. The dosages of a pharmaceutical composition disclosed herein may be adjusted when combined to achieve desired effects. On the other hand, dosages of the pharmaceutical compositions and various therapeutic agents may be independently optimized and combined to achieve a synergistic result wherein the pathology is reduced more than it would be if either was used alone.

In particular, toxicity and therapeutic efficacy of a pharmaceutical composition disclosed herein may be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effect is the therapeutic index and it may be expressed as the ratio LD50/ED50. Pharmaceutical compositions exhibiting large therapeutic indices are preferred except when cytotoxicity of the composition is the activity or therapeutic outcome that is desired. Although pharmaceutical compositions that exhibit toxic side effects may be used, a delivery system can target such compositions to the site of affected tissue in order to minimize potential damage to uninfected cells and, thereby, reduce side effects. Generally, the pharmaceutical compositions of the present invention may be administered in a manner that maximizes efficacy and minimizes toxicity.

Data obtained from cell culture assays and animal studies may be used in formulating a range of dosages for use in humans. The dosages of such compositions lie preferably within a range of circulating concentrations that include the ED50 with little or no toxicity. The dosage may vary within this range depending upon the dosage form employed and the route of administration utilized. For any composition used in the methods of the invention, the therapeutically effective dose may be estimated initially from cell culture assays. A dose may be formulated in animal models to achieve a circulating plasma concentration range that includes the IC50 (the concentration of the test composition that achieves a half-maximal inhibition of symptoms) as determined in cell culture. Such information may be used to accurately determine useful doses in humans. Levels in plasma may be measured, for example, by high performance liquid chromatography.

Moreover, the dosage administration of the compositions of the present invention may be optimized using a pharmacokinetic/pharmacodynamic modeling system. For example, one or more dosage regimens may be chosen and a pharmacokinetic/pharmacodynamic model may be used to determine the pharmacokinetic/pharmacodynamic profile of one or more dosage regimens. Next, one of the dosage regimens for administration may be selected which achieves the desired pharmacokinetic/pharmacodynamic response based on the particular pharmacokinetic/pharmacodynamic profile. See WO 00/67776, which is entirely expressly incorporated herein by reference.

More specifically, the pharmaceutical compositions may be administered in a single daily dose, or the total daily dosage may be administered in divided doses of two, three, or four times daily. In the case of oral administration, the daily dosage of the compositions may be varied over a wide range from about 0.1 ng to about 1,000 mg per patient, per day. The range may more particularly be from about 0.001 ng/kg to 10 mg/kg of body weight per day, about 0.1-100 μg, about 1.0-50 μg or about 1.0-20 mg per day for adults (at about 60 kg).

The daily dosage of the pharmaceutical compositions may be varied over a wide range from about 0.1 ng to about 1000 mg per adult human per day. For oral administration, the compositions may be provided in the form of tablets containing from about 0.1 ng to about 1000 mg of the composition or 0.1, 0.2, 0.5, 1.0, 2.0, 5.0, 10.0, 15.0, 100, 150, 200, 250, 300, 350, 400, 450, 500, 550, 600, 650, 700, 800, 900, or 1000 milligrams of the composition for the symptomatic adjustment of the dosage to the patient to be treated. An effective amount of the pharmaceutical composition is ordinarily supplied at a dosage level of from about 0.1 ng/kg to about 20 mg/kg of body weight per day. In one embodiment, the range is from about 0.2 ng/kg to about 10 mg/kg of body weight per day. In another embodiment, the range is from about 0.5 ng/kg to about 10 mg/kg of body weight per day. The pharmaceutical compositions may be administered on a regimen of about 1 to about 10 times per day.

In the case of injections, it is usually convenient to give by an intravenous route in an amount of about 0.0001 μg-30 mg, about 0.01 μg-20 mg or about 0.01-10 mg per day to adults (at about 60 kg). In the case of other animals, the dose calculated for 60 kg may be administered as well.

Doses of a pharmaceutical composition of the present invention can optionally include 0.0001 μg to 1,000 mg/kg/administration, or 0.001 μg to 100.0 mg/kg/administration, from 0.01 μg to 10 mg/kg/administration, from 0.1 μg to 10 mg/kg/administration, including, but not limited to, 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 and/or 100-500 mg/kg/administration or any range, value or fraction thereof, or to achieve a serum concentration of 0.1, 0.5, 0.9, 1.0, 1.1, 1.2, 1.5, 1.9, 2.0, 2.5, 2.9, 3.0, 3.5, 3.9, 4.0, 4.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 20, 12.5, 12.9, 13.0, 13.5, 13.9, 14.0, 14.5, 4.9, 5.0, 5.5, 5.9, 6.0, 6.5, 6.9, 7.0, 7.5, 7.9, 8.0, 8.5, 8.9, 9.0, 9.5, 9.9, 10, 10.5, 10.9, 11, 11.5, 11.9, 12, 12.5, 12.9, 13.0, 13.5, 13.9, 14, 14.5, 15, 15.5, 15.9, 16, 16.5, 16.9, 17, 17.5, 17.9, 18, 18.5, 18.9, 19, 19.5, 19.9, 20, 20.5, 20.9, 21, 22, 23, 24, 25, 26, 27, 28, 29, 30, 35, 40, 45, 50, 55, 60, 65, 70, 75, 80, 85, 90, 96, 100, 200, 300, 400, 500, 600, 700, 800, 900, 1000, 1500, 2000, 2500, 3000, 3500, 4000, 4500, and/or 5000 μg/ml serum concentration per single or multiple administration or any range, value or fraction thereof.

As a non-limiting example, treatment of subjects can be provided as a one-time or periodic dosage of a composition of the present invention 0.1 ng to 100 mg/kg such as 0.0001, 0.001, 0.01, 0.1 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively or additionally, at least one of week 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52, or alternatively or additionally, at least one of 1, 2, 3, 4, 5, 6, 7, 8, 9, 10, 11, 12, 13, 14, 15, 16, 17, 18, 19, or 20 years, or any combination thereof, using single, infusion or repeated doses.

Specifically, the pharmaceutical compositions of the present invention may be administered at least once a week over the course of several weeks. In one embodiment, the pharmaceutical compositions are administered at least once a week over several weeks to several months. In another embodiment, the pharmaceutical compositions are administered once a week over four to eight weeks. In yet another embodiment, the pharmaceutical compositions are administered once a week over four weeks.

More specifically, the pharmaceutical compositions may be administered at least once a day for about 2 days, at least once a day for about 3 days, at least once a day for about 4 days, at least once a day for about 5 days, at least once a day for about 6 days, at least once a day for about 7 days, at least once a day for about 8 days, at least once a day for about 9 days, at least once a day for about 10 days, at least once a day for about 11 days, at least once a day for about 12 days, at least once a day for about 13 days, at least once a day for about 14 days, at least once a day for about 15 days, at least once a day for about 16 days, at least once a day for about 17 days, at least once a day for about 18 days, at least once a day for about 19 days, at least once a day for about 20 days, at least once a day for about 21 days, at least once a day for about 22 days, at least once a day for about 23 days, at least once a day for about 24 days, at least once a day for about 25 days, at least once a day for about 26 days, at least once a day for about 27 days, at least once a day for about 28 days, at least once a day for about 29 days, at least once a day for about 30 days, or at least once a day for about 31 days.

Alternatively, the pharmaceutical compositions may be administered about once every day, about once every 2 days, about once every 3 days, about once every 4 days, about once every 5 days, about once every 6 days, about once every 7 days, about once every 8 days, about once every 9 days, about once every 10 days, about once every 11 days, about once every 12 days, about once every 13 days, about once every 14 days, about once every 15 days, about once every 16 days, about once every 17 days, about once every 18 days, about once every 19 days, about once every 20 days, about once every 21 days, about once every 22 days, about once every 23 days, about once every 24 days, about once every 25 days, about once every 26 days, about once every 27 days, about once every 28 days, about once every 29 days, about once every 30 days, or about once every 31 days.

The pharmaceutical compositions of the present invention may alternatively be administered about once every week, about once every 2 weeks, about once every 3 weeks, about once every 4 weeks, about once every 5 weeks, about once every 6 weeks, about once every 7 weeks, about once every 8 weeks, about once every 9 weeks, about once every 10 weeks, about once every 11 weeks, about once every 12 weeks, about once every 13 weeks, about once every 14 weeks, about once every 15 weeks, about once every 16 weeks, about once every 17 weeks, about once every 18 weeks, about once every 19 weeks, about once every 20 weeks.

Alternatively, the pharmaceutical compositions of the present invention may be administered about once every month, about once every 2 months, about once every 3 months, about once every 4 months, about once every 5 months, about once every 6 months, about once every 7 months, about once every 8 months, about once every 9 months, about once every 10 months, about once every 11 months, or about once every 12 months.

Alternatively, the pharmaceutical compositions may be administered at least once a week for about 2 weeks, at least once a week for about 3 weeks, at least once a week for about 4 weeks, at least once a week for about 5 weeks, at least once a week for about 6 weeks, at least once a week for about 7 weeks, at least once a week for about 8 weeks, at least once a week for about 9 weeks, at least once a week for about 10 weeks, at least once a week for about 11 weeks, at least once a week for about 12 weeks, at least once a week for about 13 weeks, at least once a week for about 14 weeks, at least once a week for about 15 weeks, at least once a week for about 16 weeks, at least once a week for about 17 weeks, at least once a week for about 18 weeks, at least once a week for about 19 weeks, or at least once a week for about 20 weeks.

Alternatively the pharmaceutical compositions may be administered at least once a week for about 1 month, at least once a week for about 2 months, at least once a week for about 3 months, at least once a week for about 4 months, at least once a week for about 5 months, at least once a week for about 6 months, at least once a week for about 7 months, at least once a week for about 8 months, at least once a week for about 9 months, at least once a week for about 10 months, at least once a week for about 11 months, or at least once a week for about 12 months.

The pharmaceutical compositions may further be combined with one or more additional therapeutic agents. A combination therapy regimen may be additive, or it may produce synergistic results (e.g., in a particular disease, greater than expected for the combined use of the two agents).

The compositions can be administered simultaneously or sequentially by the same or different routes of administration. The determination of the identity and amount of the pharmaceutical compositions for use in the methods of the present invention can be readily made by ordinarily skilled medical practitioners using standard techniques known in the art. In specific embodiments, an AT-1 modulator of the present invention can be administered in combination with an effective amount of another therapeutic agent, depending on the disease or condition being treated. In particular embodiments, the other therapeutic agent can be another treatment for autism spectrum disorder (e.g., cholesterol).

In various embodiments, the AT-1 modulator of the present invention in combination with an another therapeutic agent may be administered at about the same time, less than 1 minute apart, less than 2 minutes apart, less than 5 minutes apart, less than 30 minutes apart, 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, the AT-1 modulator of the present invention in combination with another therapeutic agent are cyclically administered. Cycling therapy involves the administration of a first therapy (e.g., the AT-1 modulator) for a period of time, followed by the administration of a second therapy (e.g., another therapeutic agent) for a period of time, optionally, followed by the administration of perhaps a third therapy for a period of time and so forth, and repeating this sequential administration, e.g., the cycle, in order to reduce the development of resistance to one of the therapies, to avoid or reduce the side effects of one of the therapies, and/or to improve the efficacy of the therapies. In certain embodiments, the administration of the combination therapy of the present invention may be repeated and the administrations may be separated by at least 1 day, 2 days, 3 days, 5 days, 10 days, 15 days, 30 days, 45 days, 2 months, 75 days, 3 months, or at least 6 months.

VI. SSRI MODULATORS AND METHODS OF USE

It is understood that the methods and compositions of the present invention, insofar as they are described in the context of AT-1 modulators (modulator types, screening assays, methods of use, pharmaceutical compositions, and the like) also apply in the context of selective serotonin uptake inhibitors (SSRI) to treat autism spectrum disorders and disorder in which neurogenesis is impaired. SSRI are known in the art and specifically include, but are not limited to, fluoxetine, fluvoxamine, paroxetine, sertraline and mianserin.

VII. DETECTION OF AT-1 ANTIBODY (MCAD-IgG) BIOMARKERS

A. Detection by Mass Spectrometry

In one aspect, the biomarkers of the present invention may be detected by mass spectrometry, a method that employs a mass spectrometer to detect gas phase ions. Examples of mass spectrometers are time-of-flight, magnetic sector, quadrupole filter, ion trap, ion cyclotron resonance, Orbitrap, hybrids or combinations of the foregoing, and the like.

In particular embodiments, the biomarkers of the present invention are detected using selected reaction monitoring (SRM) mass spectrometry techniques. Selected reaction monitoring (SRM) is a non-scanning mass spectrometry technique, performed on triple quadrupole-like instruments and in which collision-induced dissociation is used as a means to increase selectivity. In SRM experiments two mass analyzers are used as static mass filters, to monitor a particular fragment ion of a selected precursor ion. The specific pair of mass-over-charge (m/z) values associated to the precursor and fragment ions selected is referred to as a "transition" and can be written as parent m/z→fragment m/z (e.g. 673.5→534.3). Unlike common MS based proteomics, no mass spectra are recorded in a SRM analysis. Instead, the detector acts as counting device for the ions matching the selected transition thereby returning an intensity distribution over time. Multiple SRM transitions can be measured within the same experiment on the chromatographic time scale by rapidly toggling between the different precursor/fragment pairs (sometimes called multiple reaction monitoring, MRM). Typically, the triple quadrupole instrument cycles through a series of transitions and records the signal of each transition as a function of the elution time. The method allows for additional selectivity by monitoring the chromatographic coelution of multiple transitions for a given analyte. The terms SRM/MRM are occasionally used also to describe experiments conducted in mass spectrometers other than triple quadrupoles (e.g. in trapping instruments) where upon fragmentation of a specific precursor ion a narrow mass range is scanned in MS2 mode, centered on a fragment ion specific to the precursor of interest or in general in experiments where fragmentation in the collision cell is used as a means to increase selectivity. In this application the terms SRM and MRM or also SRM/MRM can be used interchangeably, since they both refer to the same mass spectrometer operating principle. As a matter of clarity, the term MRM is used throughout the text, but the term includes both SRM and MRM, as well as any analogous technique, such as e.g. highly-selective reaction monitoring, hSRM, LC-SRM or any other SRM/MRM-like or SRM/MRM-mimicking approaches performed on any type of mass spectrometer and/or, in which the peptides are fragmented using any other fragmentation method such as e.g. CAD (collision-activated dissociation (also known as CID or collision-induced dissociation), HCD (higher energy CID), ECD (electron capture dissociation), PD (photodissociation) or ETD (electron transfer dissociation).

In another specific embodiment, the mass spectrometric method comprises matrix assisted laser desorption/ionization time-of-flight (MALDI-TOF MS or MALDI-TOF). In another embodiment, method comprises MALDI-TOF tandem mass spectrometry (MALDI-TOF MS/MS). In yet another embodiment, mass spectrometry can be combined with another appropriate method(s) as may be contemplated by one of ordinary skill in the art. For example, MALDI-TOF can be utilized with trypsin digestion and tandem mass spectrometry as described herein.

In an alternative embodiment, the mass spectrometric technique comprises surface enhanced laser desorption and ionization or "SELDI," as described, for example, in U.S. Pat. Nos. 6,225,047 and 5,719,060. Briefly, SELDI refers to a method of desorption/ionization gas phase ion spectrometry (e.g. mass spectrometry) in which an analyte (here, one or more of the biomarkers) is captured on the surface of a SELDI mass spectrometry probe. There are several versions of SELDI that may be utilized including, but not limited to, Affinity Capture Mass Spectrometry (also called Surface-Enhanced Affinity Capture (SEAC)), and Surface-Enhanced Neat Desorption (SEND) which involves the use of probes comprising energy absorbing molecules that are chemically bound to the probe surface (SEND probe). Another SELDI method is called Surface-Enhanced Photolabile Attachment and Release (SEPAR), which involves the use of probes having moieties attached to the surface that can covalently bind an analyte, and then release the analyte through breaking a photolabile bond in the moiety after exposure to light, e.g., to laser light (see, U.S. Pat. No. 5,719,060). SEPAR and other forms of SELDI are readily adapted to detecting a biomarker or biomarker panel, pursuant to the present invention.

In another mass spectrometry method, the biomarkers can be first captured on a chromatographic resin having chromatographic properties that bind the biomarkers. For example, one could capture the biomarkers on a cation exchange resin, such as CM Ceramic HyperD F resin, wash the resin, elute the biomarkers and detect by MALDI. Alternatively, this method could be preceded by fractionating the sample on an anion exchange resin before application to the cation exchange resin. In another alternative, one could fractionate on an anion exchange resin and detect by MALDI directly. In yet another method, one could capture the biomarkers on an immuno-chromatographic resin that comprises antibodies that bind the biomarkers, wash the resin to remove unbound material, elute the biomarkers from the resin and detect the eluted biomarkers by MALDI or by SELDI.

B. Detection by Immunoassay

In other embodiments, the biomarkers of the present invention can be detected and/or measured by immunoassay. Immunoassay requires biospecific capture reagents, such as antibodies, to capture the biomarkers. Many antibodies are available commercially. Antibodies also can be produced by methods well known in the art, e.g., by immunizing animals with the biomarkers. Biomarkers can be isolated from samples based on their binding characteristics. Alternatively, if the amino acid sequence of a polypeptide biomarker is known, the polypeptide can be synthesized and used to generate antibodies by methods well-known in the art.

The present invention contemplates traditional immunoassays including, for example, sandwich immunoassays including ELISA or fluorescence-based immunoassays, immunoblots, Western Blots (WB), as well as other enzyme immunoassays. Nephelometry is an assay performed in liquid phase, in which antibodies are in solution. Binding of the antigen to the antibody results in changes in absorbance, which is measured. In a SELDI-based immunoassay, a biospecific capture reagent for the biomarker is attached to the surface of an MS probe, such as a pre-activated protein chip array. The biomarker is then specifically captured on the biochip through this reagent, and the captured biomarker is detected by mass spectrometry.

Although antibodies are useful because of their extensive characterization, any other suitable agent (e.g., a peptide, an aptamer, or a small organic molecule) that specifically binds a biomarker of the present invention is optionally used in place of the antibody in the above described immunoassays. For example, an aptamer that specifically binds all neurogranin and/or one or more of its breakdown products might be used. Aptamers are nucleic acid-based molecules that bind specific ligands. Methods for making aptamers with a particular binding specificity are known as detailed in U.S. Pat. Nos. 5,475,096; 5,670,637; 5,696,249; 5,270,163; 5,707,796; 5,595,877; 5,660,985; 5,567,588; 5,683,867; 5,637,459; and 6,011,020.

C. Detection by Electrochemicaluminescent Assay

In several embodiments, the biomarker biomarkers of the present invention may be detected by means of an electrochemicaluminescent assay developed by Meso Scale Discovery (Gaithersrburg, Md.). Electrochemiluminescence detection uses labels that emit light when electrochemically stimulated. Background signals are minimal because the stimulation mechanism (electricity) is decoupled from the signal (light). Labels are stable, non-radioactive and offer a choice of convenient coupling chemistries. They emit light at ~620 nm, eliminating problems with color quenching. See U.S. Pat. Nos. 7,497,997; 7,491,540; 7,288,410; 7,036,946; 7,052,861; 6,977,722; 6,919,173; 6,673,533; 6,413,783; 6,362,011; 6,319,670; 6,207,369; 6,140,045; 6,090,545; and 5,866,434. See also U.S. Patent Applications Publication No. 2009/0170121; No. 2009/006339; No. 2009/0065357; No. 2006/0172340; No. 2006/0019319; No. 2005/0142033; No. 2005/0052646; No. 2004/0022677; No. 2003/0124572; No. 2003/0113713; No. 2003/0003460; No. 2002/0137234; No. 2002/0086335; and No. 2001/0021534.

D. Other Methods for Detecting Biomarkers

The biomarkers of the present invention can be detected by other suitable methods. Detection paradigms that can be employed to this end include optical methods, electrochemical methods (voltametry and amperometry techniques), atomic force microscopy, and radio frequency methods, e.g., multipolar resonance spectroscopy. Illustrative of optical methods, in addition to microscopy, both confocal and non-confocal, are detection of fluorescence, luminescence, chemiluminescence, absorbance, reflectance, transmittance, and birefringence or refractive index (e.g., surface plasmon resonance, ellipsometry, a resonant mirror method, a grating coupler waveguide method or interferometry).

Furthermore, a sample may also be analyzed by means of a biochip. Biochips generally comprise solid substrates and have a generally planar surface, to which a capture reagent (also called an adsorbent or affinity reagent) is attached. Frequently, the surface of a biochip comprises a plurality of addressable locations, each of which has the capture reagent bound there. Protein biochips are biochips adapted for the capture of polypeptides. Many protein biochips are described in the art. These include, for example, protein biochips produced by Ciphergen Biosystems, Inc. (Fremont, Calif.), Invitrogen Corp. (Carlsbad, Calif.), Affymetrix, Inc. (Fremong, Calif.), Zyomyx (Hayward, Calif.), R&D Systems, Inc. (Minneapolis, Minn.), Biacore (Uppsala, Sweden) and Procognia (Berkshire, UK). Examples of such protein biochips are described in the following patents or published patent applications: U.S. Pat. Nos. 6,537,749; 6,329,209; 6,225,047; 5,242,828; PCT International Publication No. WO 00/56934; and PCT International Publication No. WO 03/048768.

E. Assays of Antibodies to AT-1

The present invention provides compositions and methods for using AT-1 proteins, polypeptides or peptides. In several embodiments, the AT-1 polypeptides described herein can be used to assay for the presence of corresponding AT-1 antibodies. In a specific embodiment, a method for detecting the presence of antibodies to AT-1 in a subject comprises contacting a biological sample taken from a subject with an AT-1 polypeptide, and detecting the binding of the polypeptide with an antibody specific for the polypeptide, wherein the detection of binding is indicative of the presence of AT-1 antibodies in the subject. The present invention contemplates the detection of antibodies to AT-1, isoforms thereof, post-translationally modified forms thereof, or combinations of any of the foregoing.

Methods for assaying such AT-1 antibodies are described herein in and known to those of ordinary skill in the art. For example, an immunoassay can be used to detect and analyze AT-1 antibodies in a biological sample. As used herein, the term "immunoassay" is used in reference to any method in which antibodies are used in the detection of an antigen. It is contemplated that a range of immunoassay formats be encompassed by this definition, including but not limited to, direct immunoassays, indirect immunoassays, and "sandwich immunoassays." However, it is not intended that the present invention be limited to any particular format. It is contemplated that other formats, including radioimmunoassays (RIA), immunofluorescent assays (IFA), and other assay formats, including, but not limited to, variations on the ELISA, RIA and/or IFA methods will be useful in the methods of the present invention. The term also includes immunoprecipitation and immunoblotting.

Thus, in one aspect, the methods of the present invention include using a sandwich assay to detect the AT-1 antibodies. Sandwich assays generally involve the use of two binding agents, e.g., antibodies, each capable of binding to a different portion, or epitope, of the protein(s) to be detected and/or quantitated. In a sandwich assay, the analyte is typically bound by a first binding agent which is immobilized on a solid support, and thereafter a second binding agent binds to the analyte, thus forming an insoluble complex. See, e.g., U.S. Pat. No. 4,376,110. Alternatively, the sandwich assay may be performed in solution, also referred to as a homogeneous assay. See, e.g., U.S. Pat. No. 7,413,862.

In some embodiments of these methods, a capture probe including a first binding agent is capable of specifically binding to an AT-1 polypeptide, which is bound to one or more AT-1 antibodies. In turn, the detection probe including a second binding agent binds to the AT-1 antibodies. Thus, in this particular example, a four-part complex is formed between: (1) the capture probe, (2) the AT-1 polypeptide, (3) the AT-1 antibody, and (4) the detection probe. In an alternative embodiment, the positions of the first and second binding agents are reversed, such that the capture probe attached to the solid support is capable of specifically binding to the AT-1 antibodies and the detection probe is capable of specifically binding to the AT-1 polypeptide or mimic thereof.

As stated above, the methods can be performed using any immunological technique known to those skilled in the art of immunochemistry. As examples, ELISA, immunofluorescence, radioimmunoassays or similar techniques may be utilized. In general, an appropriate capture probe is immobilized on a solid surface and the sample to be tested (e.g., human serum) is brought into contact with the capture probe. For example, modified glass substrates that covalently or non-covalently bind proteins can be used to bind the antigen. The substrate may be treated with suitable blocking agents to minimize non-specific binding. If the AT-1 antibody is present in the sample, a complex between the antibody and the capture probe is formed.

In another embodiment, the methods comprise contacting a sample with a capture probe capable of binding to the AT-1 antibody. The sample is also contacted with a detection probe. The presence, absence, and/or amount of the complex may be detected, wherein the presence or absence of the complex is indicative of the presence or absence of the AT-1 antibodies.

The complex can then be detected or quantitatively measured using methods well-known in the art. The detection probe may be labeled with biochemical markers such as, for example, a nanoparticle, horseradish peroxidase (HRP) or alkaline phosphatase (AP), and detection of the complex can be achieved by the addition of a substrate for the enzyme which generates a calorimetric, chemiluminescent or fluorescent product. Alternatively, the presence of the complex may be determined by addition of a marker protein labeled with a detectable label, for example an appropriate enzyme. In this case, the amount of enzymatic activity measured is inversely proportional to the quantity of complex formed and a negative control is needed as a reference to determine the presence of antigen in the sample. Another method for detecting the complex may utilize antibodies or antigens that have been labeled with radioisotopes followed by measure of radioactivity.

The sample may be contacted with the detection probe before, after, or simultaneously with the capture probe. In one embodiment, the sample is first contacted with the detection probe so that AT-1 antibodies present in the sample bind to the detection probe to form a target analyte complex. The mixture is then contacted with the substrate having capture probes bound thereto so that the target analyte complex binds to the capture probe on the substrate. In another embodiment, the sample is first contacted with the substrate so that a target analyte complex present in the sample binds to a capture probe, and the target analyte complex bound to the capture probe is then contacted with the detection probe so that the AT-1 antibodies bind to the detection probe. In another embodiment, the sample, the detection probe and the capture probe on the substrate are contacted simultaneously.

VIII. KITS

Also within the scope of the invention are kits comprising the compositions of the invention and instructions for use. In one embodiment, the kit comprises a detection reagent for detecting AT-1 specific antibody in women and/or offspring. In particular embodiments, the detection reagent is AT-1, an AT-1 receptor mimetic, and the like. The kit can further contain a least one additional reagent, or one or more additional antibodies. Kits typically include a label indicating the intended use of the contents of the kit. The term label includes any writing, or recorded material supplied on or with the kit, or which otherwise accompanies the kit.

The kit may comprise a solid support, such as a chip, microtiter plate (e.g., a 96-well plate), bead, or resin having biomarker (AT-1 antibody) capture reagents attached thereon. The kit may further comprise a means for detecting the biomarkers, such as antibodies, and a secondary antibody-signal complex such as horseradish peroxidase (HRP)-conjugated goat anti-rabbit IgG antibody and tetramethyl benzidine (TMB) as a substrate for HRP.

The kit may be provided as an immuno-chromatography strip comprising a membrane on which the antibodies are immobilized, and a means for detecting, e.g., gold particle bound antibodies, where the membrane, includes NC membrane and PVDF membrane. The kit may comprise a plastic plate on which a sample application pad, gold particle bound antibodies temporally immobilized on a glass fiber filter, a nitrocellulose membrane on which antibody bands and a secondary antibody band are immobilized and an absorbent pad are positioned in a serial manner, so as to keep continuous capillary flow of blood serum.

The kit can also comprise a washing solution or instructions for making a washing solution, in which the combination of the capture reagents and the washing solution allows capture of the biomarkers on the solid support for subsequent detection by, e.g., antibodies, mass spectrometry and the like. In a further embodiment, a kit can comprise instructions for suitable operational parameters in the form of a label or separate insert. For example, the instructions may inform a consumer about how to collect the sample, how to wash the probe or the particular biomarkers to be detected, etc. In yet another embodiment, the kit can comprise one or more containers with biomarker samples, to be used as standard(s) for calibration.

Without further elaboration, it is believed that one skilled in the art, using the preceding description, can utilize the present invention to the fullest extent. The following examples are illustrative only, and not limiting of the remainder of the disclosure in any way whatsoever.

EXAMPLES

The following examples are put forth so as to provide those of ordinary skill in the art with a complete disclosure and description of how the compounds, compositions, articles, devices, and/or methods described and claimed herein are made and evaluated, and are intended to be purely illustrative and are not intended to limit the scope of what the inventors regard as their invention. Efforts have been made to ensure accuracy with respect to numbers (e.g., amounts, temperature, etc.) but some errors and deviations should be accounted for herein. Unless indicated otherwise, parts are parts by weight, temperature is in degrees Celsius or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Materials and Methods

Collection and Purification of Maternal Antibodies. IgG was isolated from de-identified pooled serum samples of 63 mothers of children with autistic disorder (MCAD-IgG) and 63 mothers of unaffected children (MUC-IgG) who were participants in a previously published study[15]. An equal quantity of serum (225 μl) from each subject in the cohort, was pooled, filtered, and the IgG was isolated by passage over a protein A cartridge (Sigma, St Louis, Mo.) per manufacturer's protocol. IgG was eluted from the column using an acidic solution (Elution buffer) and then immediately passed over a desalting cartridge to set the eluate to physiological pH in phosphate buffered saline (PBS). Purified IgG was then filtered (0.22 μm) and maintained at 4° C.

Cell Cultures. Reagents for cell culture were purchased from Invitrogen (Carlsbad, Calif.) if not otherwise specified. Human NPC were cultured as published previously[24] in accordance with NIH guidelines and following approval by the Institutional Review Board at Johns Hopkins University and the National Institutes of Health. Briefly, human fetal brain specimens of 7-8 weeks gestation were obtained from Birth Defects Research Laboratory, University of Washington, Seattle. The tissues were then triturated into single cells after removing meninges and blood vessels. After centrifugation at 1000 rpm, cells were resuspended in DMEM/F12 media [containing 1× N2 supplement, 1% (v/v) antibiotics, 0.1% (w/v) albumin (Sigma, St. Louis, Mo.), recombinant human fibroblast growth factor-beta (hFGFb; 20 ng/mL) and human epidermal growth factor (hEGF) (20 ng/mL)] and plated onto poly-D-lysine (Sigma) coated T-25 cm$^2$ tissue culture flasks. When cell cultures reached 60% confluence, they were subcultured by vigorous shaking followed by triturating and plated at a density of 2×10$^4$ cells/ml onto poly-D-lysine coated 96 well plates or cover slips in 24 well plates. Medium was replaced every other day. NSC cultures were ready for experiments 4-5 days after replating and >98% of the cells expressed the neural stem cell marker, nestin while <1% of the cells expressed glial fibrillary acidic protein (GFAP, a marker for astrocytes) or beta-III tubulin (a neuronal cell marker) as determined by immunocytochemistry.

HEK293 cells were cultured in 6 well plates in DMEM medium containing 10% (v/v) fetal bovine serum (FBS, Gemini, West Sacramento, Calif.). The cells were transfected with Myc-DDK tagged AT-1 plasmid (Origene, Rockville, Md.) for 48 hours. Cells lysates were then collected using RIPA buffer (1% NP-40, 0.1% SDS, 50 mM Tris-HCl pH 7.4, 150 mM NaCl, 0.5% Sodium Deoxycholate, 1 mM EDTA and complete protease inhibitor cocktail (Roche, Manheim, Germany)

Cytotoxicity Assays. Cytotoxicity was determined by using CellQuanti-Blue Cell Viability Assay kit (BioAssay Systems) as previously published[24]. Briefly, NSCs were cultured in poly-D-lysine coated 96-well plates and used for experiments at ~60% confluence. MCAD and corresponding MUC (final concentrations 1:500~1:50) treatments were then applied to the cells in growth factor free maintaining media. After 24 hours, CellQuanti-Blue solution (10 μl/well) was added and the cells were incubated for 1 hour. The fluorescence was quantified at an excitation wavelength of 530 nm and emission wavelength of 590 nm using a fluorescence plate reader.

Cell Proliferation and Differentiation Assays. Cell proliferation was assessed by BrdU incorporation. The cells were first treated with MCAD or control antibodies for 18 hours and then for 6 hours with BrdU (Sigma) followed by immunostaining for BrdU. When subjected to differentiation, media was replaced with DMEM/F12 containing 2% FBS. The NPC were capable of differentiating into neurons (40-60%) and astrocytes (20-50%) after 4-7 days.

Immunocytochemistry. Cells were fixed in 4% (w/v) paraformaldehyde and permeabilized by incubation in 0.5% (v/v) Triton X-100 in PBS (PBS-T) for 20 min. For BrdU staining, the cells were also denatured in 2N HCl at 37° C. for 30 min and rinsed twice in 0.1 M sodium borate, pH 8.5. Cells were immunostained using monoclonal anti-BrdU (1:1000; Sigma-Aldrich), monoclonal anti-β-III-tubulin (1:1000; Promega), rabbit anti-GFAP (1:1000; Sigma-Aldrich), monoclonal anti-AT-1 (1:50; Abcam, Cambridge Mass.) or rabbit anti-active caspase-3 (1:1000; Sigma-Aldrich), followed by corresponding secondary antibodies (anti-rabbit Alexa Fluor 488, 1:400; anti-mouse Alexa Fluor 597, 1:400; Invitrogen) and 4',6-diamidino-2-phenylindole (DAPI) for nuclear staining. Images were acquired on a Zeiss LSM 510 META multiphoton confocal system (Carl Zeiss).

Immunoprecipitation and Western Blot Analysis. Dynabeads Protein G immunoprecipitation kit (Invitrogen) was used for immunoprecipitation according to manufacturer's instructions. Briefly, MCAD and MUC antibody bead complexes were made by mixing 5 ug of antibodies with 50 ul of Dynabead for 10 min at room temperature. Human fetal NSC were lysed using RIPA buffer. After centrifugation at 14,000 r.p.m. for 20 min, the supernatant was collected and incubated with MCAD or MUC antibody column at 4° C. overnight. The beads were washed three times with washing buffer. After discarding the supernatants, SDS loading buffer was added to the beads and the mixtures were heated at 70° C. for 10 min. The proteins were then separated by 10% (w/v) Tris-glycine polyacrylamide gels and transferred to polyvinylidene difluoride (PVDF) membranes. The membranes were blocked with 5% (w/v) BSA (Sigma) and incubated with monoclonal antibody against AT-1 (1:400) overnight at 4° C. After washing, the membranes were incubated with peroxidase-linked anti-rabbit or anti-mouse IgG (1:5000; GE health) for 1 hour at room temperature. ECL reagents (GE Health) were used for detection.

AT-1 Antibody Screening. Individual serum samples from MCAD (n=81) and MUC (n=80) were used for screening for antibodies to AT-1 using cell lysates from HEK293 cells transfected with Myc-DDK tagged AT-1 plasmid (Origene). Proteins purified from lysates from AT-1 transfected or non-transfected HEK293 cells were resolved (20 ug/lane) on a NuPAGE 4-12% Bis-Tris gel (Invitrogen) and transferred to a PVDF membrane. The membrane was cut into strips with each containing a single lane of control cell lysate and AT-1 transfected lysate and each strip was incubated with an individual serum sample (1:50; v/v) overnight in a cold room. The strips were then washed and incubated with HRP-conjugated secondary antibodies. The strips were imaged using a Fluorchem M imager (ProteinSimple, Santa Clara, Calif.) after development. Monoclonal anti-DDK antibody (Origene)—was used as a control. Select serum samples of MCAD (n=10) and MUC (n=10) were also tested by Western blot analysis using recombinant AT-1 protein (Novus Biologicals, Littleton, Colo.) as an antigen.

Statistics. Statistical analysis was performed using PRISM version 3.0. Differences were determined using Student's t test, Z-test for proportion and one-way ANOVA or two-way ANOVA for multiple comparisons. Two-tailed p-values less than 0.05 were considered significant.

Results

Figure 1C:
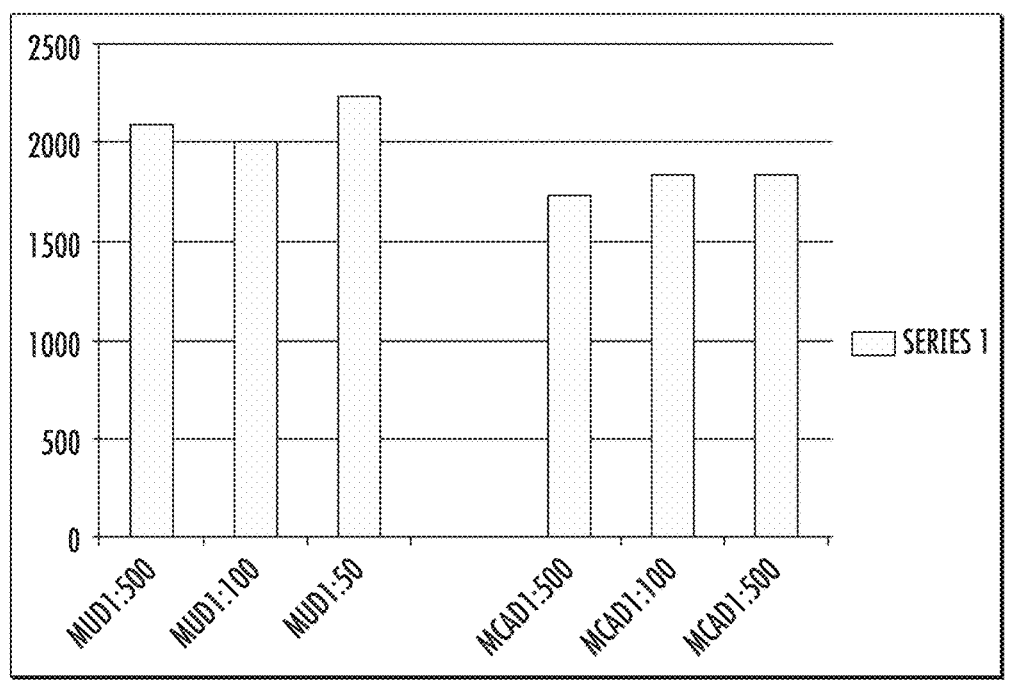
FIG. 1C. Cell toxicity was also evaluated using cellquanti-blue assay. To exclude the effect of cell proliferation, NSC cultures were treated with MCAD- or MUC-IgG in growth factors free maintaining media for 24 hours before the cellquanti-blue solution was added. No significant difference was observed between MCAD- and MUC-IgG treatments. Results are from three independent experiments.

MCAD-IgG Inhibits NSC Proliferation. The effect of MCAD on NSC proliferation was studied by exposing cultured human NSC to corresponding concentrations (1:500 to 1:50) of MCAD or MUC antibodies for 24 hours in the presence of BrdU for the last 6 hours. The number of proliferating cells were determined by calculating the percentage of BrdU immunopositive cells. MCAD-IgG treatment decreased BrdU incorporation in NSC in a concentration-dependent manner and at concentration 1:50, MCAD-IgG treatment showed significant difference compared to MUC-IgG treatment group ($p<0.05$) (FIGS. 1A and B). Another group of NSC similarly treated with the MCAD or MUC antibodies were also immunostained for active-caspase-3 to determine if MCAD-IgG could induce apoptosis in these cells. No significant caspase-3 positive cells were observed in MCAD and MUC treated groups (data not shown). Cell toxicity was also evaluated using cellquanti-blue assay. To exclude the effect of cell proliferation, NSC cultures were treated with MCAD- or MUC-IgG in growth factor-free media for 24 hours before the cellquanti-blue solution was added. No significant difference was observed between MCAD- and MUC-IgG treatments (FIG. 1C). Thus MCAD-IgG inhibited NSC proliferation without causing cell death.

Figure 2A:
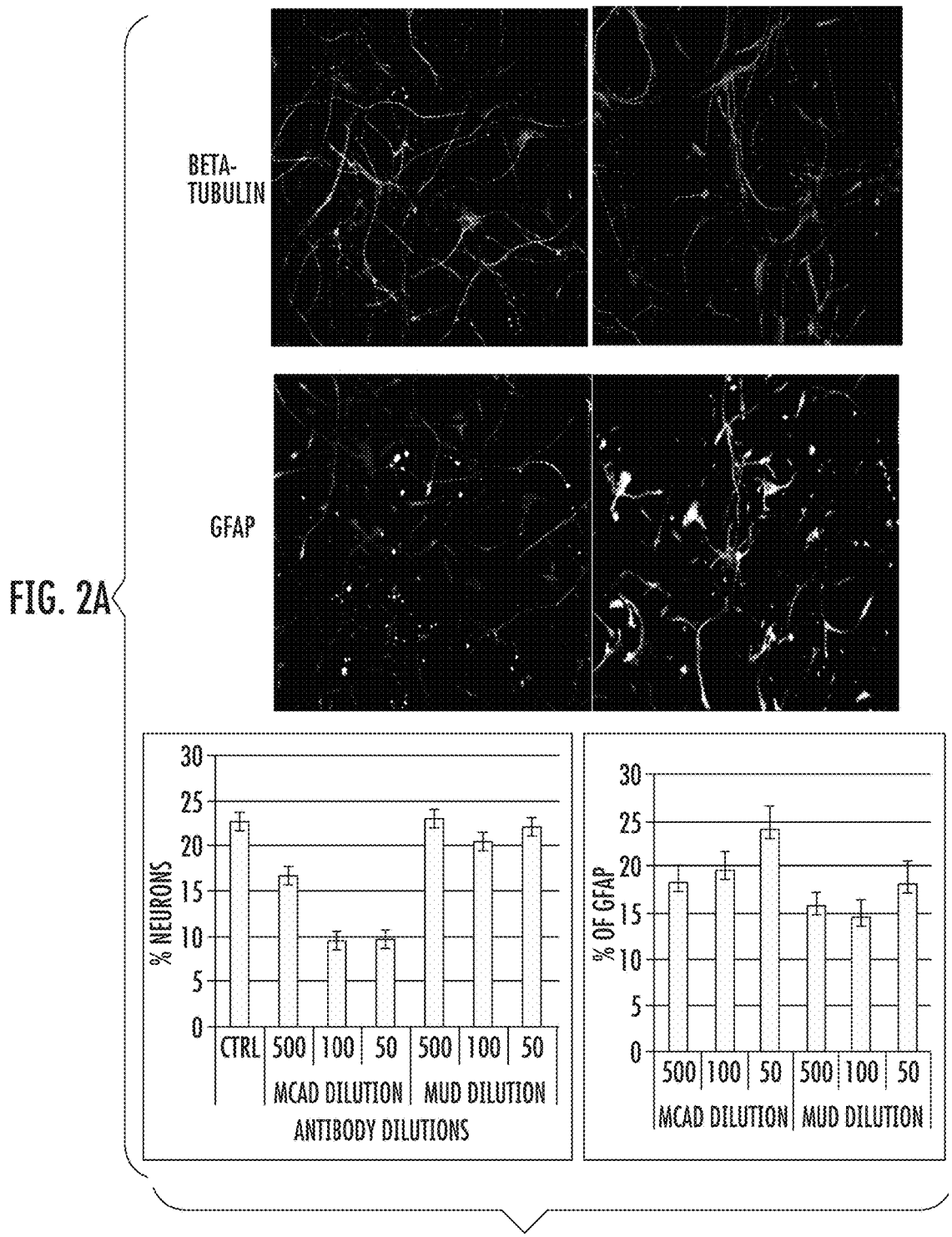
FIG. 2A. MCAD-IgG modulates neurogenesis: The effect of MCAD-IgG on NSC differentiation was studied by exposing NSC cultures to MCAD- or MUC-IgG in differentiation media for 4-7 days. NSC differentiation was studied by immunostaining the cells for neuronal marker beta-III tubulin and astroglial marker GFAP. The percentage of beta-III tubulin positive cells was used as a marker for neuronal differentiation while the percentage of GFAP positive cells was used as a marker for astroglial differentiation. MCAD-IgG treatment decreased beta-III tubulin positive cells but increased GFAP positive cells compared to MUC-IgG.
Figure 2B:
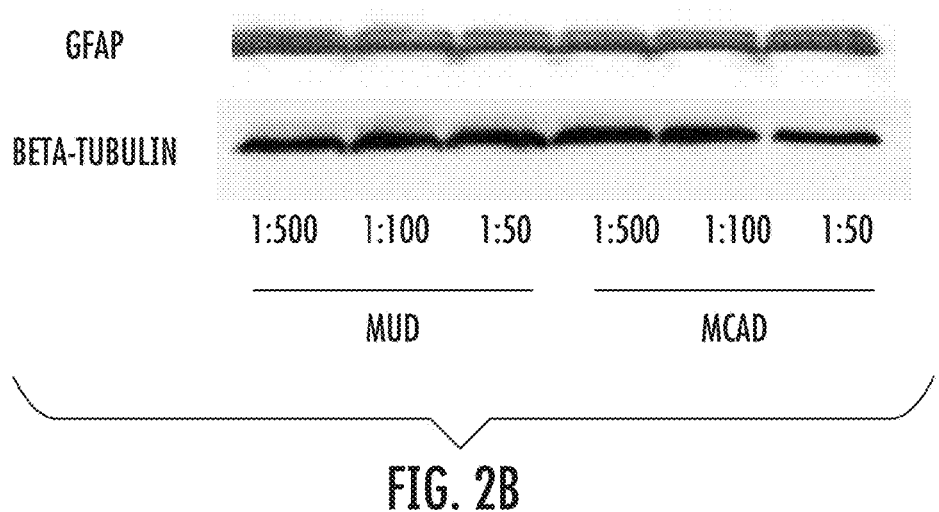
FIG. 2B. Results are from three independent experiments. MCAD-IgG treatment also caused morphological changes in GFAP positive cells compared to MUC-IgG.
Figure 2C:
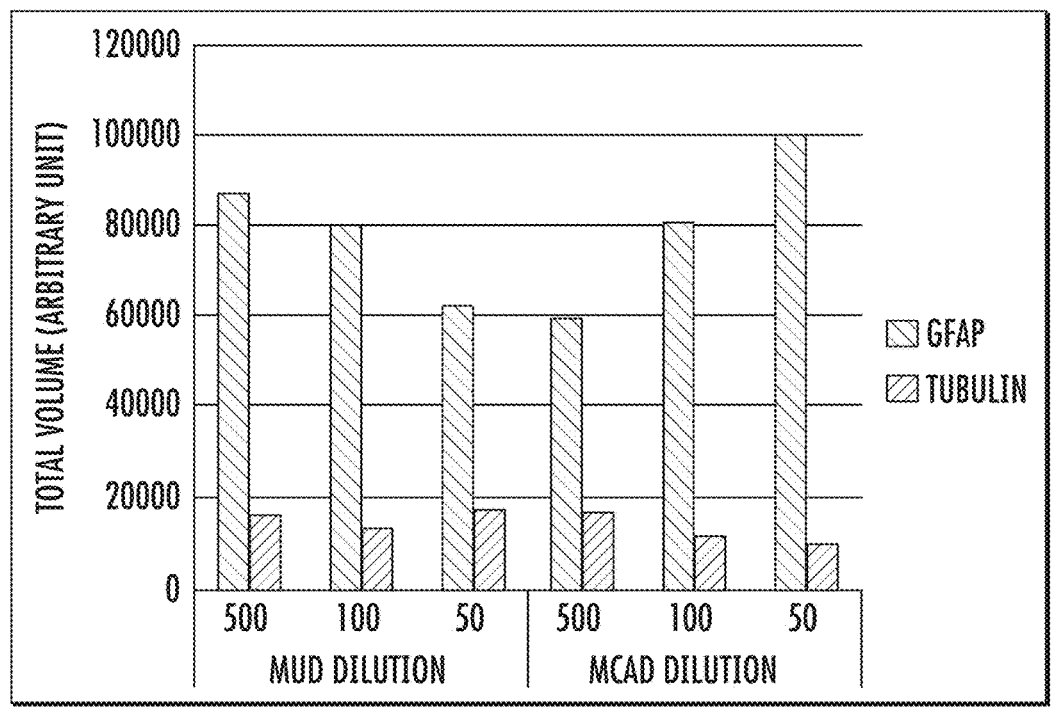
FIG. 2C. In another group of cells, after 24 hour of MCAD- or MUC-IgG treatment in differentiation media, the cells were lysized and Western blot was performed to determine the effect of MCAD-IgG on beta-III tubulin and GFAP protein productions.

Effect of MCAD-IgG on NSC Differentiation. The effect of MCAD-IgG on NSC differentiation was studied by exposing NSC cultures to MCAD- or MUC-IgG in differentiation media for 4-7 days. The percentage of beta-III tubulin positive cells was used as a marker for neuronal differentiation while the percentage of GFAP positive cells was used as a marker for astroglial differentiation. MCAD-IgG decreased the percentage of beta-III tubulin cells but increased the percentage of GFAP-positive cells compared to MUC-IgG ($p<0.05$, FIG. 2A). Some GFAP positive cells also showed significant morphological changes, showing enlarged cell bodies and enhanced GFAP immunostaining (FIG. 2B). In another group of cells, after 24 hours of MCAD- or MUC-IgG treatment in differentiation media, the cells were lysized and Western blot analysis was performed to determine the effect of MCAD on beta-III tubulin and GFAP protein expression. MCAD-IgG treatment decreased beta-III tubulin but increased GFAP protein production, while MUC-IgG showed no significant effect (FIG. 2C). Thus MCAD-IgG treatment inhibited NSC neuronal differentiation but increased astroglial differentiation and activation.

Figure 3A:
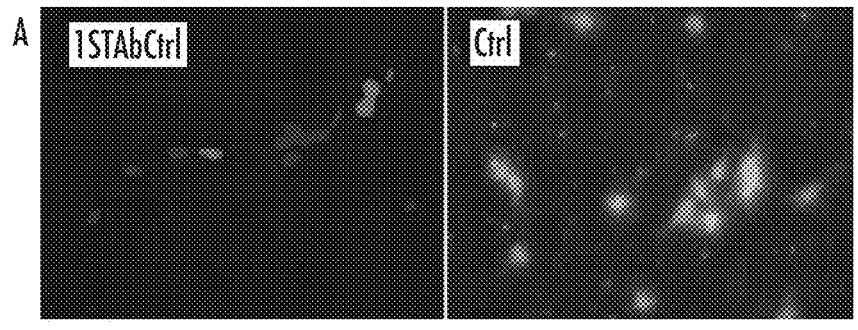
FIG. 3A. AT-1 receptor expression on NSC: To determine whether AT-1 receptor was one of the epitopes on the cell membrane that MCAD-IgG interacted with, we first immunostained the NSC with a monoclonal antibody against AT-1 receptor.
Figure 3B:
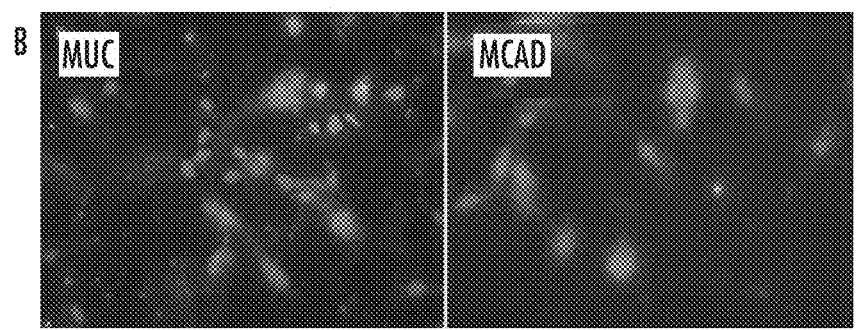
FIG. 3B. i), control staining without first antibody incubation; ii) AT-1 expression on NSC. AT-1 immunostaining was significantly lower in NSC transfected with siRNA specific to AT-1 compared to negative control small RNA (Nsi) No significant difference was observed between NSC treated with MCAD and MUC antibodies.
Figure 3C:
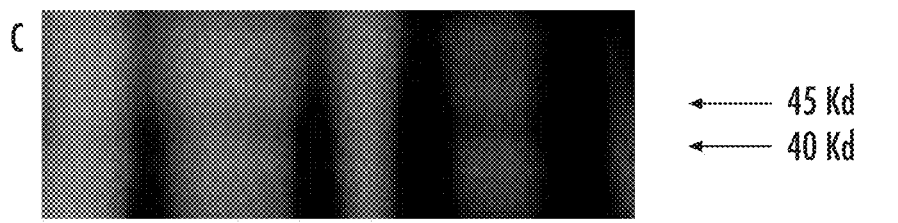
FIG. 3C. Immunoprecipitation of AT-1. NSC cell lysates were immunoprecipitated with MCAD-IgG protein G Dyna beads first, the precipitated proteins were then eluted and Western blot was used to detect AT-1 receptor in the elution using a monoclonal antibody against AT-1.

MCAD-IgG Targets AT-1 Receptor on NPC. To determine whether AT-1 receptor was expressed in NSC, we first immunostained these cells with a monoclonal antibody against the AT-1 receptor and found prominent expression of the receptor on the cell surface (FIG. 3A). The expression of this receptor could be blocked by siRNA against AT-1 but no effect was seen following treatment with either MCAD-IgG or MUC-IgG (FIG. 3B). We then determined if AT-1 could be recognized by MCAD-IgG. NSC cell lysates were immunoprecipitated with MCAD-IgG conjugated to protein G Dyna beads. The precipitated proteins were eluted and analyzed by Western blots using a monoclonal antibody against AT-1. As shown in FIG. 3C, a 40 kD AT-1 band was immunoprecipitated by MCAD-IgG although some immune reactivity was also seen with MUC-IgG. To further confirm the existence of AT-1 antibody in MCAD serum, we used AT-1 transfected HEK293 cell lysates to screen for AT-1 antibodies in individual serum samples (81 from MCAD and 80 from MUD). Seventeen samples from MCAD contained antibodies against 40 kD AT-1 band, compared to only four samples from MUC (data not shown). The significance was significant using Z-test. We also tested a small group of individual serum (10 each from MCAD and MUC) for their abilities to recognize recombinant AT-1 bands transferred on a PVDF membrane. One MCAD serum recognized the 40 kD AT-1 band (data not shown). These results indicate MCAD contains antibody/antibodies targeting AT-1 receptor.

Screen of AT-1 Antibodies in Maternal Serum. Cell lysates purified from AT-1 plasmid transfected HEK293 cells and non-transfected control cells were used to further screen AT-1 antibodies in 81 MCAD and 80 MUC maternal sera. Strips containing non-transfected and AT-1 transfected proteins were incubated with individual serum before HRP-conjugated secondary antibody incubation. A representative image showing a serum sample recognized 40 Kd AT-1 band in AT-1 transfected cell lysate (data not shown). Recombinant AT-1 protein was also used to confirm the existence of AT-1 antibodies in selected samples. A representative image showed a MCAD serum reacted with the recombinant AT-1 protein but a MUC serum did not (data not shown).

Figure 4A:
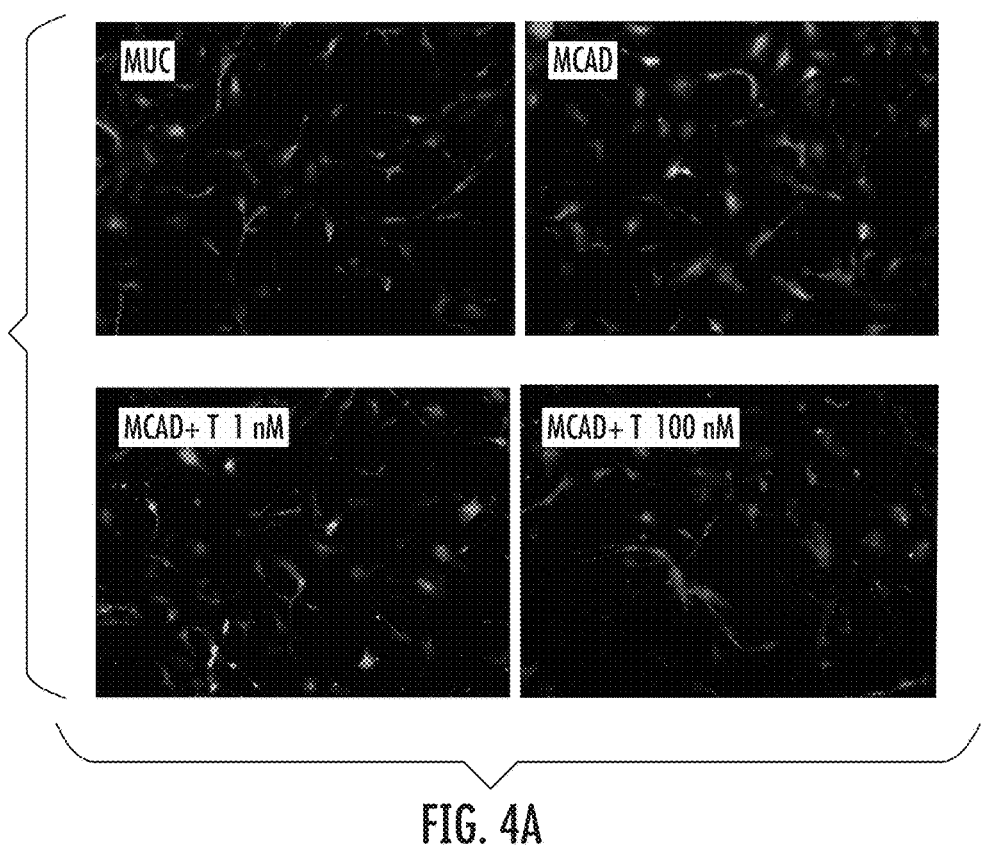
FIG. 4A-4C. Modulation of AT-1 activation attenuates MCAD-IgG inhibited neurogenesis: AT-1 inhibitor telmisartan (T, 1-10 nM) was used to treat NSC 30 min prior to IgG treatments. NSC differentiation was studied by immunostaining the cells for neuronal marker beta-III tubulin and astroglial marker GFAP after 4-7 d of IgG treatments. The percentage of beta-III tubulin positive cells was used as a marker for neuronal differentiation while the percentage of GFAP positive cells was used as a marker for astroglial differentiation (A). Results were from three independent experiments. Toxicity of higher concentration of telmisartan was observed using cellquanti-blue assay (B). NSC were also transfected with siRNA specific to AT-1 for 24 hours before MCAD-IgG treatment and differentiation. The cell differentiation was then determined using the above mentioned method (C).
Figure 4B:
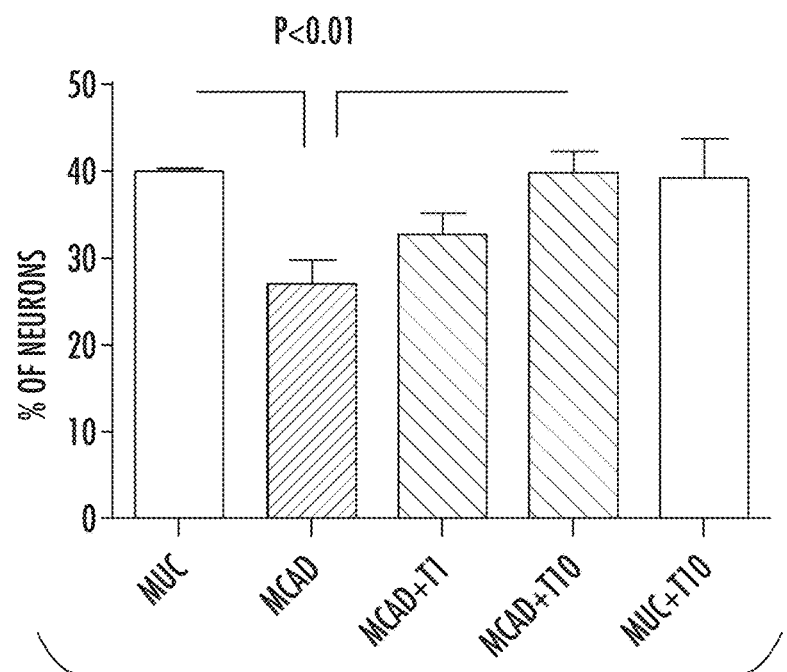
Figure 4C:
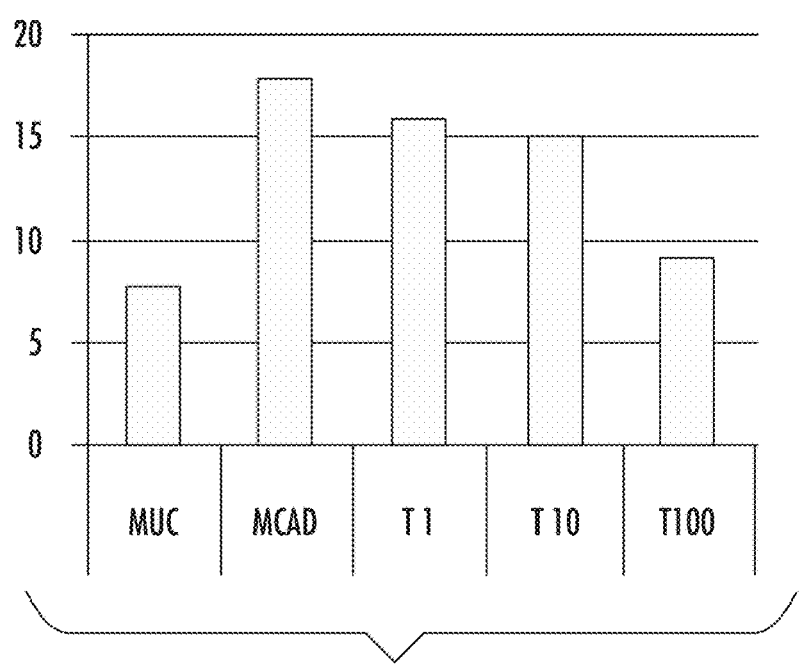
Figure 5:
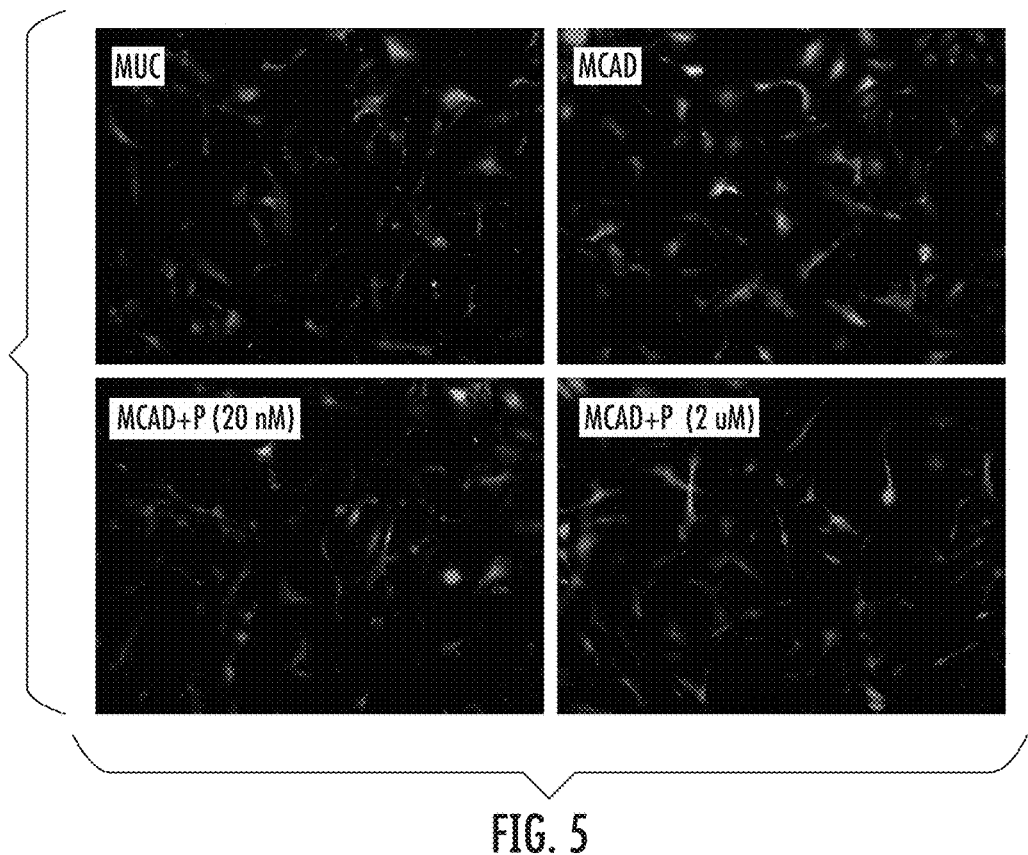
FIG. 5. Paroxetine protects NSC against MCAD effect on neurogenesis: NSC cultures in differentiation media were pretreated with paroxetine (P, 20 nM-2000 nM) 1 hour prior to MCAD-IgG (1:50) or MUC-IgG treatment. The neurogenesis was determined after 4 days using immunostaining for beta-III tubulin and GFAP. The percentage of beta-III tubulin positive cells was used as a marker for neuronal generation and the percentage of GFAP positive cells was used as a marker for astroglial generation. Results are presented as Mean±SEM, from three independent experiments.

Modulation of AT-1 activation attenuates MCAD-IgG inhibited neurogenesis. To determine whether inhibition of AT-1 receptor could attenuate effects of MCAD-IgG on NPC, these cells were pretreated with an AT-1 inhibitor, Telmisartan for 30 min prior to IgG treatments. Telmisartan (10 nM) pretreatment significantly attenuated MCAD-IgG caused effect on neuronal and astroglial differentiation (FIG. 4A). However, higher concentrations (10-100 uM) of telmisartan caused toxicity in cells as determined by cellquantiblue (FIG. 4B). Further, siRNAs against AT-1 inhibited AT-1 expression (FIG. 3A) and partially attenuated MCAD-IgG caused effect on astroglial differentiation (FIG. 4C). These results indicate that AT-1 plays an important role in NSC differentiation and may be responsible, at least partially, for MCAD-induced effect on neuronal and astroglial differentiation.

Paroxetine Protects NSC Against MCAD Effect on Neurogenesis. As SSRIs have been reported to improve some symptoms of autism[25], we tested whether SSRI attenuate MCAD-IgG induced effect on neurogenesis. NSC cultures in differentiation media were pretreated with paroxetine (20 nM-2 uM) 1 hour prior to MCAD-IgG (1:50) treatment. Neurogenesis was determined after 4 days using immunostaining for beta-III tubulin and GFAP. As shown in FIG. 4, Paroxetine pretreatment reversed MCAD-IgG caused inhibition of neurogenesis and enhanced astroglial differentiation. These results indicate that SSRI can be used to protect NSC against effects of MCAD-IgG.

Discussion

In the present study, we determined the effects of MCAD-IgG on the survival, proliferation and differentiation of NSC. We found that MCAD-IgG inhibits NSC proliferation and neuronal differentiation, but increases astroglial differentiation and activation. This effect was at least partially mediated by activating the AT-1 receptor on the NSC membrane. Furthermore, an SSRI, paroxetine, countered the effects of MCAD-IgG on neurogenesis.

Presence of abnormal serum antibodies in autistic disorder children or mothers with autistic children has been reported[3,14,15,26,27]. While no specific childhood antibody against fetal brain antigens in children with autism could predict autism[28], independent studies have found specific circulating antibodies that target fetal brain epitopes in a subset of mothers with autistic children. For the antibodies reactive against human fetal brain proteins of a molecular mass of 36 kDa, more MCAD samples had antibodies (10%) than control mothers (2%). For a 39 kDa antigen, MCAD-IgG had a denser band on Western blot (possibly high concentration of specific antibodies, maybe better affinity) than MUC-IgG, though the number of individual samples reactive against this antigen were comparable (14 vs. 15)[15,29]. A correlation between maternal antibodies against fetal brain proteins in the 36-39 kDa range and the presence of developmental regression in affected offsprings has also been established[14,15]. As maternal antibodies can cross the placenta, they may directly affect fetal brain development and contribute to the pathogenesis of autistic disorders. In a pregnant mouse model, it was observed that the passive transfer of MCAD-IgG changed the expression of cytokines and caused microglial activation in the embryo brains and induced alterations of sociability in offsprings at adolescence without gross anatomical changes in the brain[16].

In the present study, we determined the effect of MCAD-IgG on NSC using our well established human NSC cultures. Compared to in vivo systems, where the inherent protective mechanisms in normal brain environment may prevent observable pathological changes, lacking complex interactions with other cells makes the simple NSC culture an ideal model to study MCAD-IgG induced effects and decipher the underlying mechanisms. We observed that MCAD-IgG inhibited NSC proliferation and neuronal differentiation while it increased astroglial differentiation. The enhanced GFAP expression in MCAD-IgG treated NSC is in agreement with a previous report which observed marked activation of astroglia in the brain of autistic patients[30]. We did not observe any effect of MCAD-IgG on cell viability and apoptosis of NSC. However the MCAD-IgG induced impairment of NSC proliferation and differentiation may be a major hindrance to brain development and may contribute to the pathogenesis of autism.

We next determined the underlying mechanisms by which MACD-IgG alters NSC functions. We identified specific membrane epitopes and intracellular pathways by which MCAD-IgG act on NSC. We studied membrane proteins that have known effects on stem cell functions with molecular mass of 37-40 KD. One of the proteins AT1, is a G protein coupled receptor with angiotensins as its ligand, which is widely expressed in brain[31]. Although AT-1 expression and function has not been yet studied on neural stem/progenitor cells, AT-1 function has been related to cell fate determination and is involved in the neuronal K+ and Ca2+ modulation[32,33]. Its activation inhibits human endothelial progenitor cells proliferation[34,35] but enhances mouse pleuripotent stem cell proliferation and mesodermal progenitor differentiation[36], suggesting that AT-1 if expressed in NSC, may also play a role in neural progenitor cell proliferation and differentiation. Furthermore, abnormal brain AT-1 receptor activity has been associated with increased stress, anxiety and depression and brain inflammation which may lead to neuronal injury[37-39]. Angiotensin stimulation itself can also increase AT-1 receptor expression on mouse neuronal cell line through activating the transcription factors nuclear factor-κB (NF-κB) and Ets-like protein 1 (Elk-1)[40]. A recent report shows that AT-1 receptor activation may induce neurotoxicity by acting directly on neurons or indirectly through astroglial activation[41, 42]. The neuroprotective effect by inhibition of brain AT-1 receptor activity has been observed in both animal models and in humans[41-43]. It has been suggested that blockade of AT-1 receptors could be a novel therapeutic approach for mood disorders and neurodegenerative diseases of the brain[44]. Interestingly, autoantibodies against AT-1 are not unusual in pregnant women. As reported, an activating antibody against the second extracellular loop of the angiotensin II type 1 receptor was found in 28 serum samples from 58 pre-eclamptic patients, while the same antibody was found in two of 51 samples from normal controls. The IgG from the patients significantly constricted both the villus veins and arteries in a dose-dependent manner in vitro, which could be blocked by the AT-1 receptor antagonist losartan[45]. It has been suggested that maternal pre-eclampsia or eclampsia is significantly associated with autism spectrum disorders in an analysis of 87,677 births from 1996 through 2002, insured by the South Carolina Medicaid program[46]. In another report, the activating AT-1 antibody was found responsible for renal-allograft rejection[47].

We found that AT-1 receptor was expressed on NSC. Both AT-1 specific siRNA and low dose AT-1 inhibitor, telmisartan, attenuated the effect of MCAD-IgG, which contains antibodies specific against AT-1, on neurogenesis and astroglial activation. The effect of AT-1 on enhanced astroglial activation is in agreement with previous report that AT-1 activation may enhance cultured rat astroglial growth[48]. The mechanism of AT-1 inhibited neuronal differentiation is unknown. However, it has been reported that AT-1 activates Rho/Rho-kinase pathway[49], which is a critical pathway regulating neuronal differentiation and maturation[50, 51] and likely plays a role in the AT-1 inhibited neurogenesis, which needs to be further studied. Using immunoprecipitation, we found that although both MUC and MCAD-IgG co-immunoprecipitated with 40 kd AT-1, The MCAD-IgG immunoprecipitates higher density of the receptor and also with a 45 Kd AT-1 form, also in much lesser density. This observation indicates that MCAD-IgG may contain a unique AT-1 antibody which recognizes different forms of AT-1, as compared to MUC-IgG. Furthermore, when using telmisartan, high affinity AT1 blocker antagonists, it significantly attenuated MCAD-IgG effect on NSC differentiation. Though at higher concentration, the inhibitor showed cell toxicity. Our results indicate MCAD-IgG can target NSC, likely against membrane bound proteins including AT-1, causing significant inhibition of neurogenesis.

Although we found that AT-1 receptor at least partially responsible for the observed effect of MCAD-IgG caused effect and Telmisartan may reverse the effect in lower concentration in our system. However, the observation that at higher concentration, telmisartan itself may also cause cell toxicity make it not suitable for therapy. Furthermore, the discrepancy between the observed molecular weights in different reports indicates that it is also possible that MCAD-IgG as a mixture of antibodies can target multiple membrane proteins on NSC. There are still concerns that MCAD-IgG alone is enough to cause autism. For example, although mothers having autistic children with developmental regression were more likely to have serum antibody reactivity against human fetal brain at 36 and 39 kDa, mothers with unaffected children also have reactivity to similar epitopes. Additionally, despite reporting that five multiplex mothers had serum antibodies at 61 kDa and solely affected offspring, MCAD possessing similar antibodies had normal offspring following the birth of an autistic child[28]. Hence, we speculate that although MCAD-IgG has potential to harm brain targets including NSC, dysfunctions in other parties, especially those with protective functions, may be also required to lead the MCAD-IgG caused-toxicity to fully developed autism. Thus, a common intracellular pathway that mediates inhibitory effects on NSC proliferation and differentiation may be more feasible target for treatment. Serotonergic dysfunction has been observed in autism cases and may play a role in autism. As normal serotonergic system may provide protection to NSC, and disruption of early serotonergic neuronal development might be involved in the etiology of autism[20]. SSRIs such as fluoxetine and paroxetine have been used successfully for treatment of selective autism symptoms such as anxiety and depression and have shown the added benefit of increasing social interaction and inhibiting repetitive behavior[25, 52]. More interestingly, it has also been reported that SSRIs increase NSC number in the human dentate gyrus (DG) in major depressive disorder[53]. In our preliminary in vitro study, we also observed that paroxetine increased proliferation of NSC in a concentration-dependent manner. These findings suggest that serotonergic dysfunction may attribute to NSC damage, and on the other hand, SSRIs treatment may benefit on autism through enhancing NSC function. Thus, it is interesting to know whether SSRI treatment can attenuate MCAD-IgG caused dysfunction in NSC. We tested the effect of pretreatment of SSRIs, in accordance with the literature, SSRIs treatment also provided benefit in autism patients besides its effect on ES stem cells, indicating its enhancement in NSC proliferation may be a general effect which can compensate the MCAD-IgG caused loss in NSC proliferation even after the MCAD-IgG attack. These findings suggest that SSRIs treatment may actually enhance NSC function to the benefit on autism. On the other hand, the dysfunction in serotonergic system may result in failed protection in NSC when targeted by MCAD-IgG.

Our study showed that MCAD-IgG causes decreased NSC proliferation and neuronal differentiation and enhanced astroglial reactivation. The effect of MCAD-IgG on NSC may be through targeting AT-1 receptor on the cell membrane and can be reversed by AT-1 receptor inhibition or SSRI treatment. The dysfunction of NSC caused by MCAD-IgG may contribute to the pathogenesis of autistic disorders and AT-1 receptor inhibition and SSRI could be used for therapy.

REFERENCES

1. Comi A M, Zimmerman A W, Frye V H, Law P A, Peeden J N. Familial clustering of autoimmune disorders and evaluation of medical risk factors in autism. J Child Neurol. 1999 June; 14(6):388-94.
2. Plioplys A V, Greaves A, Yoshida W. Anti-CNS antibodies in childhood neurologic diseases. Neuropediatrics. 1989 May; 20(2):93-102.
3. Singer H S, Morris C M, Williams P N, Yoon D Y, Hong J J, Zimmerman A W. Antibrain antibodies in children with autism and their unaffected siblings. Journal of neuroimmunology. 2006 September; 178(1-2):149-55.
4. Singh V K, Warren R, Averett R, Ghaziuddin M. Circulating autoantibodies to neuronal and glial filament proteins in autism. Pediatric neurology. 1997 July; 17(1): 88-90.

5. Todd R D, Ciaranello R D. Demonstration of inter- and intraspecies differences in serotonin binding sites by antibodies from an autistic child. Proceedings of the National Academy of Sciences of the United States of America. 1985 January; 82(2):612-6.

6. Lee L C, Zachary A A, Leffell M S, et al. HLA-DR4 in families with autism. Pediatric neurology. 2006 November; 35(5):303-7.

7. Rogers T, Kalaydjieva L, Hallmayer J, et al. Exclusion of linkage to the HLA region in ninety multiplex sibships with autism. Journal of autism and developmental disorders. 1999 June; 29(3):195-201.

8. Tones A R, Maciulis A, Stubbs E G, Cutler A, Odell D. The transmission disequilibrium test suggests that HLA-DR4 and DR13 are linked to autism spectrum disorder. Human immunology. 2002 April; 63(4):311-6.

9. Dalton P, Deacon R, Blamire A, et al. Maternal neuronal antibodies associated with autism and a language disorder. Annals of neurology. 2003 April; 53(4):533-7.

10. Vincent A, Dalton P, Clover L, Palace J, Lang B. Antibodies to neuronal targets in neurological and psychiatric diseases. Annals of the New York Academy of Sciences. 2003 May; 992:48-55.

11. Croen L A, Grether J K, Yoshida C K, Odouli R, Van de Water J. Maternal autoimmune diseases, asthma and allergies, and childhood autism spectrum disorders: a case-control study. Archives of pediatrics & adolescent medicine. 2005 February; 159(2):151-7.

12. Molloy C A, Morrow A L, Meinzen-Derr J, et al. Familial autoimmune thyroid disease as a risk factor for regression in children with Autism Spectrum Disorder: a CPEA Study. Journal of autism and developmental disorders. 2006 April; 36(3):317-24.

13. Sweeten T L, Bowyer S L, Posey D J, Halberstadt G M, McDougle C J. Increased prevalence of familial autoimmunity in probands with pervasive developmental disorders. Pediatrics. 2003 November; 112(5):e420.

14. Braunschweig D, Ashwood P, Krakowiak P, et al. Autism: maternally derived antibodies specific for fetal brain proteins. Neurotoxicology. 2008 March; 29(2):226-31.

15. Singer H S, Morris C M, Gause C D, Gillin P K, Crawford S, Zimmerman A W. Antibodies against fetal brain in sera of mothers with autistic children. J Neuroimmunol. 2008 February; 194(1-2):165-72.

16. Singer H S, Morris C, Gause C, Pollard M, Zimmerman A W, Pletnikov M. Prenatal exposure to antibodies from mothers of children with autism produces neurobehavioral alterations: A pregnant dam mouse model. J Neuroimmunol. 2009 Jun. 25; 211(1-2):39-48.

17. Magavi S S, Leavitt B R, Macklis J D. Induction of neurogenesis in the neocortex of adult mice. Nature. 2000 Jun. 22; 405(6789):951-5.

18. Arvidsson A, Collin T, Kirik D, Kokaia Z, Lindvall O. Neuronal replacement from endogenous precursors in the adult brain after stroke. Nat Med. 2002 September; 8(9): 963-70.

19. Hallbergson A F, Gnatenco C, Peterson D A. Neurogenesis and brain injury: managing a renewable resource for repair. J Clin Invest. 2003 October; 112(8):1128-33.

20. Miyazaki K, Narita N, Narita M. Maternal administration of thalidomide or valproic acid causes abnormal serotonergic neurons in the offspring: implication for pathogenesis of autism. Int J Dev Neurosci. 2005 April-May; 23(2-3):287-97.

21. Ingram J L, Stodgell C J, Hyman S L, Figlewicz D A, Weitkamp L R, Rodier P M. Discovery of allelic variants of HOXA1 and HOXB1: genetic susceptibility to autism spectrum disorders. Teratology. 2000 December; 62(6):393-405.

22. Martinez-Ceballos E, Gudas L J. Hoxa1 is required for the retinoic acid-induced differentiation of embryonic stem cells into neurons. Journal of neuroscience research. 2008 October; 86(13):2809-19.

23. Li H, Radford J C, Ragusa M J, et al. Transcription factor MEF2C influences neural stem/progenitor cell differentiation and maturation in vivo. Proceedings of the National Academy of Sciences of the United States of America. 2008 Jul. 8; 105(27):9397-402.

24. Wang T, Lee M H, Johnson T, et al. Activated T-cells inhibit neurogenesis by releasing granzyme B: rescue by Kv1.3 blockers. J Neurosci. 2010 April 7; 30(14):5020-7.

25. Hollander E, Soorya L, Chaplin W, et al. A double-blind placebo-controlled trial of fluoxetine for repetitive behaviors and global severity in adult autism spectrum disorders. Am J Psychiatry. 2012 March; 169(3):292-9.

26. Cabanlit M, Wills S, Goines P, Ashwood P, Van de Water J. Brain-specific autoantibodies in the plasma of subjects with autistic spectrum disorder. Annals of the New York Academy of Sciences. 2007 June; 1107:92-103.

27. Silva S C, Correia C, Fesel C, et al. Autoantibody repertoires to brain tissue in autism nuclear families. Journal of neuroimmunology. 2004 July; 152(1-2):176-82.

28. Morris C M, Zimmerman A W, Singer H S. Childhood serum anti-fetal brain antibodies do not predict autism. Pediatric neurology. 2009 October; 41(4):288-90.

29. Zimmerman A W, Connors S L, Matteson K J, et al. Maternal antibrain antibodies in autism. Brain, behavior, and immunity. 2007 March; 21(3):351-7.

30. Vargas D L, Nascimbene C, Krishnan C, Zimmerman A W, Pardo C A. Neuroglial activation and neuroinflammation in the brain of patients with autism. Annals of neurology. 2005; 57(1):67-81.

31. Thomas M A, Fleissner G, Hauptfleisch S, Lemmer B. Subcellular identification of angiotensin I/II- and angiotensin II (AT1)-receptor-immunoreactivity in the central nervous system of rats. Brain research. 2003; 962(1-2):92-104.

32. Imanishi T, Hano T, Nishio I. Angiotensin II potentiates vascular endothelial growth factor-induced proliferation and network formation of endothelial progenitor cells. Hypertens Res. 2004 February; 27(2):101-8.

33. Sumners C, Zhu M, Gelband C H, Posner P. Angiotensin II type 1 receptor modulation of neuronal K+ and Ca2+ currents: intracellular mechanisms. The American journal of physiology. 1996 July; 271(1 Pt 1):C154-63.

34. Endtmann C, Ebrahimian T, Czech T, et al. Angiotensin II Impairs Endothelial Progenitor Cell Number and Function In Vitro and In Vivo. Hypertension. 2011 Sep. 1, 2011; 58(3):394-403.

35. Pelliccia F, Pasceri V, Cianfrocca C, et al. Angiotensin II receptor antagonism with telmisartan increases number of endothelial progenitor cells in normotensive patients with coronary artery disease: A randomized, double-blind, placebo-controlled study. Atherosclerosis. 2010; 210(2):510-5.

36. Ishizuka T, Goshima H, Ozawa A, Watanabe Y. Effect of angiotensin II on proliferation and differentiation of mouse induced pluripotent stem cells into mesodermal progenitor cells. Biochemical and Biophysical Research Communications. 2012; 420(1):148-55.

37. Aguilera G, Kiss A, Luo X. Increased expression of type 1 angiotensin II receptors in the hypothalamic paraventricular nucleus following stress and glucocorticoid administration. Journal of neuroendocrinology. 1995 October; 7(10):775-83.

38. Villar-Cheda B, Valenzuela R, Rodriguez-Perez A I, Guerra M J, Labandeira-Garcia J L. Aging-related changes in the nigral angiotensin system enhances proinflammatory and pro-oxidative markers and 6-OHDA-induced dopaminergic degeneration. Neurobiology of Aging. 2010; In Press, Corrected Proof 39. Rodriguez-Pallares J, Rey P, Parga J A, Muñoz A, Guerra M J, Labandeira-Garcia J L. Brain angiotensin enhances dopaminergic cell death via microglial activation and NADPH-derived ROS. Neurobiology of Disease. 2008; 31(1):58-73.

40. Mitra A K, Gao L, Zucker I H. Angiotensin II-induced upregulation of AT1 receptor expression: sequential activation of NF-κB and Elk-1 in neurons. American Journal of Physiology—Cell Physiology. 2010 Sep. 1, 2010; 299(3): C561-C9.

41. Min L-J, Mogi M, Iwanami J, et al. Angiotensin II and aldosterone-induced neuronal damage in neurons through an astrocyte-dependent mechanism. Hypertens Res. 2011; 34(6):773-8.

42. Wu X, Kihara T, Hongo H, Akaike A, Niidome T, Sugimoto H. Angiotensin receptor type 1 antagonists protect against neuronal injury induced by oxygen-glucose depletion. British Journal of Pharmacology. 2010; 161(1):33-50.

43. Lou M, Blume A, Zhao Y, et al. Sustained Blockade of Brain AT1 Receptors Before and After Focal Cerebral Ischemia Alleviates Neurologic Deficits and Reduces Neuronal Injury, Apoptosis, and Inflammatory Responses in the Rat. J Cereb Blood Flow Metab. 2004; 24(5):536-47.

44. Saavedra J M, Sánchez-Lemus E, Benicky J. Blockade of brain angiotensin II AT1 receptors ameliorates stress, anxiety, brain inflammation and ischemia: Therapeutic implications. Psychoneuroendocrinology. 2011; 36(1):1-18.

45. Zhang S, Zheng R, Yang L, et al. Angiotensin type 1 receptor autoantibody from preeclamptic patients induces human fetoplacental vasoconstriction. Journal of Cellular Physiology. 2012:n/a-n/a.

46. Mann J R, McDermott S, Bao H, Hardin J, Gregg A. Pre-eclampsia, birth weight, and autism spectrum disorders. J Autism Dev Disord. 2010 May; 40(5):548-54.

47. Dragun D, Müller D N, Bräsen J H, et al. Angiotensin II Type 1-Receptor Activating Antibodies in Renal-Allograft Rejection. New England Journal of Medicine. 2005; 352(6): 558-69.

48. Clark M A, Tran H, Nguyen C. Angiotensin III stimulates ERK1/2 mitogen-activated protein kinases and astrocyte growth in cultured rat astrocytes. Neuropeptides. 2011; 45(5):329-35.

49. Sagara Y, Hirooka Y, Nozoe M, Ito K, Kimura Y, Sunagawa K. Pressor response induced by central angiotensin II is mediated by activation of Rho/Rho-kinase pathway via AT1 receptors. Journal of Hypertension. 2007; 25(2):399-406 10.1097/HJH.0b013e328010b87f.

50. Dottori M, Leung J, Turnley A M, Pébay A. Lysophosphatidic Acid Inhibits Neuronal Differentiation of Neural Stem/Progenitor Cells Derived from Human Embryonic Stem Cells. STEM CELLS. 2008; 26(5):1146-54.

51. Nusser N, Gosmanova E, Zheng Y, Tigyi G. Nerve Growth Factor Signals through TrkA, Phosphatidylinositol 3-Kinase, and Racl to Inactivate RhoA during the Initiation of Neuronal Differentiation of PC12 Cells. Journal of Biological Chemistry. 2002 Sep. 27, 2002; 277(39):35840-6.

52. Kolevzon A, Mathewson K A, Hollander E. Selective serotonin reuptake inhibitors in autism: a review of efficacy and tolerability. J Clin Psychiatry. 2006 March; 67(3):407-14.

53. Boldrini M, Hen R, Underwood M D, et al. Hippocampal Angiogenesis and Progenitor Cell Proliferation Are Increased with Antidepressant Use in Major Depression. Biol Psychiatry. 2012; 72(7):562-71.

We claim:

1. A method of screening a female patient for a high risk of having children with an autism spectrum disorder (ASD) comprising the steps of:
   (a) obtaining a sample from the female patient, wherein the serum is suspected of comprising an antibody to angiotensin II type 1 receptor;
   (b) contacting the serum sample obtained from the female patient with an AT-1 polypeptide;
   (c) incubating the serum sample with the AT-1 polypeptide under conditions sufficient to allow the formation of AT-1 antibody:AT-1 polypeptide complexes;
   (d) detecting the presence or absence of the AT-1 antibody:AT-1 polypeptide complexes;
   (e) identifying the female patients as having a high risk of having children with ASD if AT-1 antibody:AT-1 polypeptide complexes are detected and identifying the female patient as not having a high risk of having children with ASD if AT-1 antibody:AT-1 polypeptide complexes are not detected; and
   (f) treating the female patients identified as having a high risk of having children with ASD with an effective amount of Telmisartan, a selective serotonin reuptake inhibitor (SSRI) and/or plasmaphoresis or immunophoresis to remove the AT-1 antibodies.

2. The method of claim 1, wherein the female patient is pregnant.

3. The method of claim 1, wherein the female patient is not pregnant.

4. The method of claim 1, wherein the SSRI is fluoxetine, fluvoxamine, paroxetine, sertraline or mianserin.

* * * * *